United States Patent [19]

Kirsch et al.

[11] Patent Number: 5,443,484
[45] Date of Patent: Aug. 22, 1995

[54] TROCAR AND METHOD FOR ENDOSCOPIC SURGERY

[75] Inventors: Wolff M. Kirsch, Redlands; Yong H. Zhu, Loma Linda, both of Calif.

[73] Assignee: Loma Linda University Medical Center, Loma Linda, Calif.

[21] Appl. No.: 212,317

[22] Filed: Mar. 14, 1994

Related U.S. Application Data

[63] Continuation of Ser. No. 899,605, Jun. 16, 1992, abandoned.

[51] Int. Cl.$^6$ ............................................. A61B 17/34
[52] U.S. Cl. ................................... 604/164; 606/185
[58] Field of Search ..................... 606/185; 128/20; 604/164, 165, 166, 167, 168, 174

[56] References Cited

U.S. PATENT DOCUMENTS

| | | | |
|---|---|---|---|
| 3,308,819 | 3/1967 | Arp | 604/164 |
| 3,653,388 | 4/1972 | Tenckhoff . | |
| 3,750,667 | 8/1973 | Pshenichny et al. | 604/164 X |
| 3,856,021 | 12/1974 | McIntosh . | |
| 3,893,454 | 7/1975 | Hagelin . | |
| 3,952,742 | 4/1976 | Taylor | 604/164 X |
| 4,585,437 | 7/1986 | Simms . | |
| 4,817,587 | 4/1989 | Janese | 128/20 |
| 5,002,577 | 3/1991 | Hasson | 604/174 X |
| 5,009,643 | 4/1991 | Reich et al. . | |
| 5,122,122 | 6/1992 | Allgood | 604/174 |
| 5,147,316 | 9/1992 | Castillenti | 604/174 X |
| 5,176,128 | 1/1993 | Andrese | 128/20 |
| 5,183,464 | 2/1993 | Dubrul et al. | 604/164 X |
| 5,183,465 | 2/1993 | Xanthakos . | |
| 5,248,298 | 9/1993 | Bedi et al. . | |
| 5,261,888 | 11/1993 | Semm . | |
| 5,279,567 | 1/1994 | Ciaglia et al. . | |
| 5,330,501 | 7/1994 | Tovey et al. | 604/164 X |
| 5,353,785 | 10/1994 | Wilk | 128/20 |

FOREIGN PATENT DOCUMENTS

| | | | |
|---|---|---|---|
| 0391396 | 10/1990 | European Pat. Off. | 128/20 |
| 0487175 | 5/1992 | European Pat. Off. . | |
| 748666 | 7/1993 | France . | |
| 3321621 | 10/1984 | Germany . | |
| 3713831 | 12/1988 | Germany . | |
| 4020956 | 1/1991 | Germany | 606/185 |
| 9102553 | 5/1991 | Germany . | |
| 9106553 | 8/1991 | Germany . | |
| 2154608 | 9/1985 | United Kingdom . | |
| 1528465 | 12/1989 | U.S.S.R. | 606/185 |
| 8904638 | 6/1989 | WIPO | 606/185 |
| 9221294 | 12/1992 | WIPO . | |

OTHER PUBLICATIONS

Commercial Advertisement—"Disposal Surgiport ® and Surgineedle ® Instruments Save Money!", Auto Suture Company, 1988.
H. M. Hasson, M.D., *Technique of Open Laparoscopy*, May 1979.
"Laparoscopic Principles and Techniques," *Principles of Endoscopic Surgery*, pp. 86–91, [unknown date].
Carl A. Zucker, M.D. and Robert W. Bailey, M.D., *Atlas of Endo Cholecystectomy with Auto Suture ® Instruments*, [unknown date].

*Primary Examiner*—Michael H. Thaler
*Attorney, Agent, or Firm*—Knobbe, Martens, Olson & Bear

[57] ABSTRACT

A trocar system for assisting in the generation of ports for endoscopic surgery is disclosed in which a retractor is used to place the peritoneum in counter-traction to facilitate the penetration of the trocar. Peritoneal counter-traction results in increased surface tension which reduces the force and downward momentum necessary to achieve trocar penetration, thereby eliminating the risk of excess penetration and injury to internal organs. The retractor can taken on a variety of configurations, such as a half-cylinder design in which a distal blade is inserted beneath the deeper fascial tissues and rotated into position for releasable connection and articulation with a similar half-cylinder. The two retractor halves are then joined to form a combined guide and retractor to receive the trocar for countertraction and penetration. In another embodiment, the retractor is of an integral cylindrical design with lateral distal hooks for gripping the fascial tissues obliquely. In this embodiment, the gripping is so superior that several such retractors can be used to elevate the tissues of the patient without the need for pneumoperitoneum. An improved conical trocar tip is also disclosed.

14 Claims, 19 Drawing Sheets

TROCAR AND METHOD FOR ENDOSCOPIC SURGERY

This application is a continuation of application U.S. Ser. No. 07/899,605, Filed Jun. 16, 1992, now abandoned, entitled "Trocar for Endoscopic Surgery."

FIELD OF THE INVENTION

The present invention relates to a trocar, and, more specifically, to a trocar system having a counter-traction mechanism to aid in the penetration of the trocar into a patient's body while eliminating the risks associated with previous trocar use.

BACKGROUND OF THE INVENTION

Endoscopic surgery is a procedure by which operations on internal portions of a patient's body are performed on a minimally intrusive basis. Such surgery is accomplished by creating small incisions or ports in the patient's body through which various small, remotely controllable instruments may be manipulated. The procedure is accomplished visually with the aid of an endoscope, hence the name endoscopic surgery. Substantial advantages are realized from this form of surgery, including reduced trauma to the patient, less risk of death or complications, and rapid recovery.

The endoscope is a thin, tubular instrument utilizing fiber optics which allows a surgeon to remotely view internal body structures. As such, endoscopes typically have lenses located at an insertion or distal end, and an ocular or viewer located at the proximal end of the instrument outside of the body. Often times, the viewer takes the form of a video monitor. A light source is provided at the distal end to illuminate the internal body area. Various tools are used to perform the procedures associated with the surgery, as viewed by the endoscope. These tools often include retractors, irrigators, snippers, lasers, and the like.

Each of these tools, along with the endoscope itself, must be inserted in a patient's body through a port, as noted above. A port is comprised of an incision in the patient's body into which a hollow, tubular cannula is inserted. The cannula then serves as a conduit for receiving and supporting the endoscopic instruments.

An endoscopic port is created and the cannula is simultaneously placed therein by means of a trocar. A trocar is a surgical instrument having a sharp triangular point that enters the body through a small surgical stab incision. The cannula fits over the trocar and enters the incision along with it, such that after the port is created and the trocar is removed, the cannula remains in place to define the endoscopic port.

In a typical gallbladder surgery or cholecystectomy, as many as four to six ports must be made to accommodate the various endoscopic instruments needed to complete this procedure. Obviously, other types of endoscopic surgery will require more or fewer numbers of ports. Each port, including its associated cannula, must pass through the abdominal wall which includes the outer skin, a layer of fat, a layer of fascia or alternating muscle and fascia, and the peritoneum. The layers of fat and fascia may vary in thickness, depending upon the body location and whether the patient is asthenic or obese. Peritoneum is a strong, elastic membrane lining the walls of the abdominal cavity. Just below the peritoneum, however, lie several vital organs, such as the liver, stomach and intestines, and other sensitive tissues.

In cholecystectomies, as well as other types of endoscopic surgeries (appendectomies, etc.) a state of pneumoperitoneum is induced in the patient in order to provide an enlarged body cavity for manipulation of the endoscopic instruments and to avoid damage to internal organs and tissues. Thus, in pneumoperitoneum, the surgical area is insufflated with carbon dioxide. Insufflation is achieved initially with a so-called verese needle which is a large needle used to puncture the patient for the introduction of gas. However, some risk arises from this process in that the needle may be penetrated too far into the body, thus injuring the patient. On the other hand, if the needle does not pass at least through the abdominal wall when insufflation is initiated, other serious risks arise.

Immediately after the initial insufflation with a verese needle, a first endoscopic port is established via a trocar-guided cannula to permit internal visualization of the internal cavities. Thereafter, continued insufflation can occur through the cannula during surgery. As explained above, other endoscopic ports are necessary to accomplish the surgical procedure. Thus, the trocar, by providing a piercing guide for the cannula, which thereafter sustains pneumoperitoneum and defines a port for the surgical procedure itself, is critical to the success of endoscopic surgery.

However, the dangers of trocars are well recognized. In some cases, inadvertent visceral injury has occurred to vital organs through excessive trocar penetration. These dangers vary with the surgeon's experience, the dimensions of the trocar, and its site of insertion into the body cavity. Additional risks may arise from previous abdominal surgery, or peritonitis, in which adhesions may be responsible for complications associated with the insertion of the trocar and its associated cannula.

Thus, significant risks arise from the trocar establishment of endoscopic ports, especially the first port which is "blind." However, even with the aid of endoscopic vision, subsequent trocar insertion can also be a serious risk to the patient. This is due, in large part, to the combined toughness and elasticity of the abdominal wall which requires substantial manual force for trocar penetration. The built-up force, and subsequent momentum, which the surgeon develops in jabbing the trocar through the abdominal wall is difficult to reverse, thus leading, in some cases, to excessive penetration and injury. In order to limit the depth to which the trocar travels as it is pressed into the body, many surgeons use the ulnar border of the hand as a stop. Other surgeons press a finger along the axis of the cannula or trocar in order to limit the extent of travel. In both cases, however, the momentum of the insertion hand is simply transferred to these other limbs. This fact, combined with the flexibility of the abdominal wall which prevents it from successfully resisting penetration pressure, precludes these methods from offering an effective stop mechanism.

In order to reduce the risks of trocar usage, surgeons conventionally pinch a section of the skin with the hand not manipulating the trocar and lift it in the opposite vertical direction as the travel of the trocar. In other words, the abdominal wall is pulled upwardly with the intent of lifting the skin, fat, fascia, and peritoneum away from the vital organs below, thereby enlarging the void between the abdominal wall and such organs. This method is intended to provide a margin of error such that excessive penetration of the trocar will not reach the organs below the abdominal wall. This method, however, is also ineffective in many cases. First, it is difficult to get a good grip on the skin with the non-trocar hand, which is often the weaker hand of the surgeon. Secondly, the site of the finger pinch is, necessarily, somewhat removed from the site of the trocar insertion. Thus, only a portion or component of the lifting motion is transferred laterally to the exact location where the trocar is entering the body cavity. Thirdly, while the pinch method may be effective in asthenic persons, the thicker layers of fat in obese individuals render it highly unsatisfactory. Therefore, an improved method of trocar insertion is needed.

In light of the dangers of the above-described pinch method, specialized disposable trocars have recently been developed which are provided with spring loaded guards or shields for the sharp tip of the trocar. The shields are automatically deployed outwardly to cover the sharp tip of the trocar after abdominal wall penetration is achieved. Shield deployment, however, is sometimes delayed, and even a few milliseconds of delay can result in trocar injury. Furthermore, these trocars cost as much as several hundred dollars each and, since several must be used in a single endoscopic surgery, they result in greater expense. Thus, the use of shielded trocars is not a complete solution to this sensitive problem.

Another method for establishment of endoscopic ports, which does not require the use of a sharp trocar, is referred to as the "open laparoscopic" method. In accordance with this method, continuous visual control is maintained for insertion of a special open laparoscopic cannula. The key to this method is the use of an S-shaped retractor and Allis or Kocher type grasping forceps to laterally enlarge the initial incision and to lift the fascia. This procedure exposes the peritoneum and places it under tension so that it can be carefully pierced or incised. Although this method is relatively safe, it suffers from serious defects.

First, the procedure is lengthy and complicated, requiring a number of steps. In addition, insufflation pressure is lost due to the nature and length of time in which the port is open. Also, the port size is often larger than trocar induced ports, thus causing more discomfort and increasing recovery time for the patient. Thus, there is a need for a system of endoscopic port preparation which combines the advantages of a trocar without the attendant dangers.

SUMMARY OF THE INVENTION

The present invention addresses and solves the problems of the prior art by providing a trocar system which is securely positioned below the fascia, at the exact site of trocar insertion, which allows the surgeon to induce an upward force which counteracts the force of trocar penetration. Thus, not only is a lifting action induced which is opposite to the direction of travel of the trocar, but a state of countertraction is generated which counteracts or neutralizes the dangerous downward momentum necessary for trocar penetration. Therefore, since the penetration motion can be much more carefully controlled, the risk of internal injury is greatly diminished or eliminated.

Another important advantage of this system is that it places the peritoneum in reverse or counter-tension against excessive trocar penetration. In other words, not only does the present system lift the fascia and peritoneum away from the vital organs below in order to create a margin for avoiding injury, it does so at the precise location of trocar penetration. Thus, the strength of the peritoneum is put to use by resisting excessive travel of the trocar. At the same time, because the peritoneum is placed in tension, it is somewhat easier to penetrate. Another advantage of the present system is that it can be accomplished with a single hand. Thus, the force with which the trocar is advanced can be counteracted by a similar and opposite force for resisting excessive penetration. Because the surgeon is using the same hand for both motions, there is sensitivity and "feel" for the amount of pressure needed in both cases. On the other hand, two hands can also be successfully utilized with the system of the present invention.

Other additional advantages follow from the use of this system. First, the retractor system can be inexpensively produced. Only a standard trocar is necessary rather than costly trocars having automatic spring-biased shields. A special retractor can be inexpensively produced and is used to secure the trocar system to the deeper fascial tissues in order to permit the application of counter traction, as explained above.

Another advantage of the present system is that it can be used many times in a single surgery. Only the very tip of the trocar need to be replaced, thus providing an inexpensive system. According to the method of the present invention, after an initial stab incision, with or without lateral retraction of the incision walls, the trocar system is inserted into the incision and the retractor apparatus is placed into contact with the deep fascial layers. Then, the retractor is used to generate a direct lifting force simultaneously with the downward penetration force of the trocar. The substantial and effective lifting force also places the peritoneum in tension, making it easier for the trocar to penetrate therethrough while at the same time resisting excessive penetration. In accordance with another method of the present invention, a specialized trocar can then be utilized to endoscopically view the degree of penetration so that additional penetration can safely proceed.

The trocar system of the present invention contemplates a retractor of various designs. In one embodiment, the retractor comprises a two-part system which is releasably engageable to form a combined cannula/retractor. Each part of the retractor comprises one-half of a cylinder, a retractor blade, and a finger loop or handle for countertraction. Each retractor part is inserted into the stab incision separately so as to facilitate placement of the retractor blade beneath the facial layer. The two cylinder halves are then brought together form a complete cylinder or cannula. In this position, the retractor can produce counter-traction. The trocar, with an associated cannula, is then inserted through the retractor for peritoneal penetration, and it is then removed. In one embodiment, the cylindrical portion of the retractor is slidably mounted to the handles of the retractor to facilitate its insertion into the stab incision.

In another embodiment of the present system, a one-piece cylindrical retractor is utilized having distal teeth or hooks which engage the deep fascial tissue. This secure engagement of the deep fascial layers provides for enhanced counter-traction. In this case, the retractor engages this tissue with a twisting or cork-screw motion. Thus, unlike previous embodiments in which the actual attachment of the retractor to the deep fascial tissue is in a lateral or horizontal direction, in this embodiment the motion of the retractor which results in this engagement is primarily vertical or longitudinal.

This embodiment has the added advantage of minimizing the lateral retraction of the incision itself, thus providing a tight seal between the surrounding tissue and the retractor/trocar system to prevent the escape of insufflation gas.

This one-piece embodiment of the present invention also enjoys another advantage due to the increased tension placed on the peritoneum at the point of penetration. This increased tension is due to the improved gripping, which occurs about almost a complete 360° circumference, which is provided by the cylindrical teeth or hooks formed on the distal end of the retractor. Thus, this configuration results in less peritoneal flexing. The additional advantage from this system is that the trocar system itself can be actually fixed to the tissues, thus eliminating the need for external manual or structural support. In other words, the engagement of the distal teeth of the retractor into the deep fascial layers serves as an anchor for vertically and securely holding the trocar system in place. Thus, it is not necessary to continually manually or structurally hold the trocar in place during this procedure.

The attachment of the retractor to the fascial tissue is so secure that several such retractors can be used to retract the entire abdominal wall in the surgical field, thus eliminating the need for pneumoperitoneum. This is an important advantage since that procedure sometimes causes serious side effects. In addition, because trocar penetration can be efficiently and safely achieved, a less damaging, conical trocar is disclosed. Accordingly, surgical repair and healing are facilitated with a reduced risk of adhesion.

In all embodiments of the retractors used in connection with the present invention, the retractor can be provided with stop mechanisms as an extra security against excessive penetration. Moreover, retractors of various designs are possible with the principles of the present invention. Another important advantage of the present trocar is a provision of a small port within the trocar itself. Due to the breadth of the faces of the trocar blade, a small longitudinal trocal port or hole of approximately 6–20 millimeters can be provided therethrough. Thus, the initial penetration of the trocar tip through the abdominal wall can permit the passage of a small endoscope, on the order of 0.5 or 0.8 millimeter, through this trocal port, to visualize and inspect the area to ensure adequate penetration. In addition, a cannula bearing the endoscope can be inserted through the trocal port and into the body cavity. If desired or necessary to view the progress of insufflation, gas can be introduced into the annulus formed between the cannula walls and the endoscope. Also, the endoscope can be removed or can be left in place for subsequent supplemental insufflation. Thus, this novel trocal port eliminates the need and risk associated with the use of a verese needle.

In summary, the trocar system of the present invention presents substantial advantages over the trocars of the prior art.

DETAILED DESCRIPTION OF THE INVENTION

Figure 1:
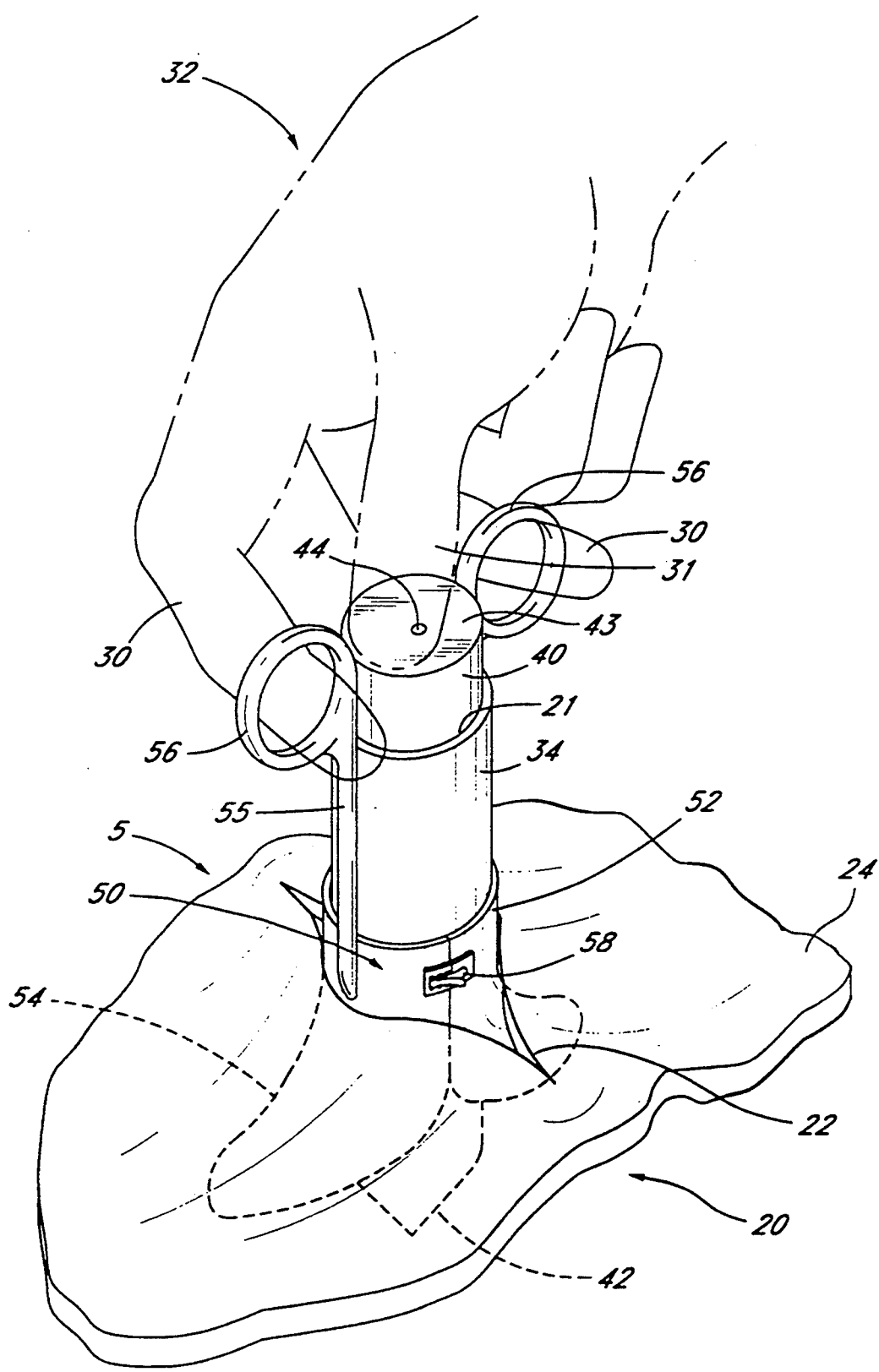
FIG. 1 is a perspective view of one embodiment of the trocar system of the present invention illustrating the manner in which a single hand of a surgeon can induce an upward force which is counter or opposite to the direction of trocar penetration.

Referring to FIG. 1 there is shown the trocar system 20 of the present invention as inserted into a stab incision 22 in the patient preparatory to the formation of a port 21 for endoscopic surgery.

The system 20 comprises the trocar 40, which is shown being pressed by the thumb 31 of the surgeon, its surrounding cannula 34 which will define the endoscopic port 21, and a retractor 50, which is retractable in an upward direction by the fingers 30 of the surgeon for providing counter-pressure to the penetration of the trocar 40. The sharp tip 42 of the trocar 40 is shown in dotted lines beneath the skin layer 24. It will be noted that the present invention is compatible with trocars of various dimension and diameters. At the external end 43 of the trocar 40 there is shown a small hole 44 which is the proximal opening of a trocal port 46 of the present invention, as is shown more completely in FIGS. 2–4. This trocal port 46 serves as a conduit for endoscopes or cannulas, as explained below in more detail.

The cannula 34 which surrounds the trocar 40 provides a conduit defining an endoscopic port 21. Through this endoscopic port 21, endoscopes and other instruments are inserted into the body cavity in order to achieve the surgical purpose. Continued insufflation of carbon dioxide gas may be sustained through the endoscopic port 21 during the procedure.

Still referring to FIG. 1, the retractor 50 component of the present system 20 is comprised of a guide portion 52, a pair of retractor blades 54 (shown in dotted lines beneath the surface of the patient's skin 24), and two handles 55 having finger loops 56 to receive the fingers 30 of the surgeon for imparting reverse motion to the system. Preferably, the retractor 50 of FIG. 1 is constructed in two halves 51a,b which are mirror images of one another and which are capable of being joined and articulated about a latch 58. The manner of inserting and articulating these two halves 51a,b of the retractor 50 are explained below in more detail and illustrated below in connection with FIGS. 5–10.

Figure 2:
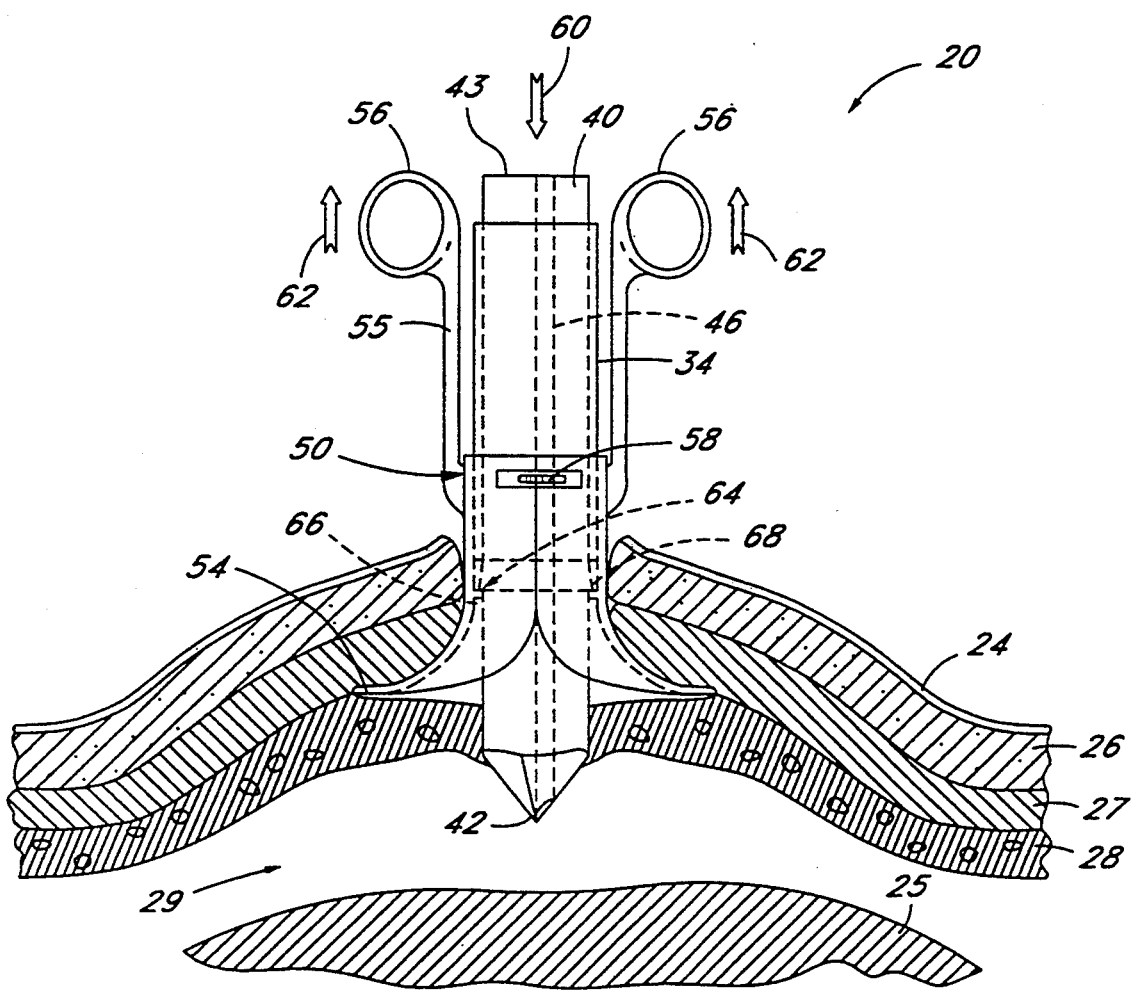
FIG. 2 is a cross-sectional view illustrating the penetration of the trocar of the body cavity as assisted by the counter-traction provided by the retractor blades inserted into the lower portion of the fascial layer.

FIGS. 1 and 2 illustrate the preferred placement of the surgeon's hand 32 in connection with the trocar 40, and the forces imparted thereon. The thumb 31 of the hand 32 rests on the proximal end 43 of the trocar 40 for providing forceful downward penetration motion 60. At the same time, the fingers 30 of the hand 32 are inserted through the loops 56 of the retractor handles 55 for providing an opposite upward force 62 on the system 20 to lift the abdominal wall of the patient's body away from vital organs 25 beneath and to minimize unnecessary downward trocar 40 penetration. In other words, it is important to note that the trocar system 20 of the present invention not only lifts the abdominal wall away from the vital organs 25 below, thereby creating a margin of safety 29, but also inherently generates a counter-motion or momentum which counteracts the downward penetration momentum of trocar 40 insertion. Thus, once penetration of the abdominal wall has been achieved, the downward momentum of penetration is simultaneously being counter-balanced and can be quickly stopped or even reversed. This presents a significant advantage over trocars of the prior art in which, once penetration was achieved, downward momentum was uncontrolled. Thus, the present trocar system 20 not only permits lifting, but also controls and counter balances downward penetration forces.

Trocar System of FIGS. 2–10

These important principles of the present invention are illustrated in FIG. 2 which is a partial cross-sectional view illustrating the placement of the trocar system 20 within the abdominal wall of the umbilicus region of a patient's body. The abdominal wall in the umbilicus region of humans encompasses the skin 24, fat 26, fascia 27, and peritoneum 28. In other regions of the body, muscle tissue is sandwiched between fascial tissues 27. The drawings showing a homogeneous fascial tissue layer 27 are considered representative of both regions. The peritoneum 28 is the strong, elastic membrane which protects the vital organs 25 below.

FIG. 2 illustrates the direction of the respective forces acting on the present trocar system 20. The downward penetration motion 60 of the trocar 40 is counter-balanced or counteracted by the upward lifting forces 62 acting on the retractor 50. Thus, the outer layers of tissue are lifted away from the vital organs 25 to provide a margin of error or safety 29 against excessive trocar 40 penetration. As shown in FIG. 2, therefor, the trocar 40 only slightly penetrates the peritoneum whereupon its downward momentum or force 60 is neutralized by the upward forces 62 acting on the retractor 50. This upward force 62 is transferred to the trocar 40 by means of an annular stop device 64 which can take the form of an annular ledge 66 formed on the interior surface of the retractor 50. This ledge 66 interferes with an annular ridge 68 formed on the exterior of the trocar 40. These components are shown in more detail and described in connection with FIGS. 3–4.

Once the trocar 40 has penetrated the peritoneum slightly, as shown in FIG. 2, an endoscope (not shown) can be inserted through the trocal port 46 in order to visualize the degree of penetration. Thereafter, the trocar 40 can be advanced carefully with the aid of endoscopic vision.

FIG. 2 illustrates the preferred placement of the retractor blades 54 beneath the deeper fascial tissues 27. This positioning of the retractor 50 improves its lifting capability even when thick layers of fat 26 are experienced, for example, in obese individuals.

Figure 3:
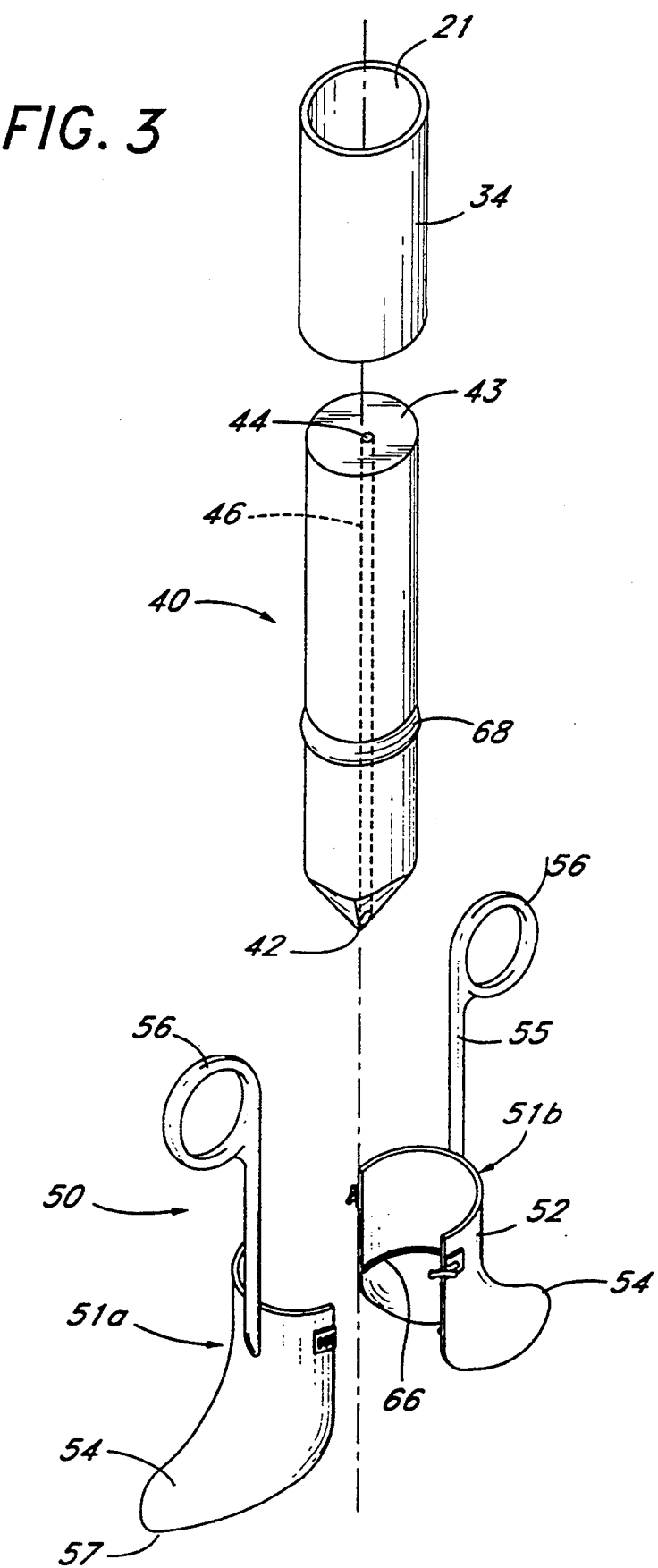
FIG. 3 is an exploded view of one embodiment of the trocar of the present invention illustrating the two-piece retractor system, the trocar, and the cannula.

FIG. 3 illustrates an exploded view of the trocar system 20 of the present invention, including the cannula 34, the trocar 40 itself and the two retractor halves 51a,b which together comprise the handle 55, guide portion 52 and blades 54 of the retractor 50. As pointed out above, the cannula 34 is slidable over the trocar 40 and remains in place as the endoscopic port 21 for the insertion of endoscopes, instruments and the like. Its use and placement will be discussed below in more detail in connection with FIGS. 5–10.

Figure 4:
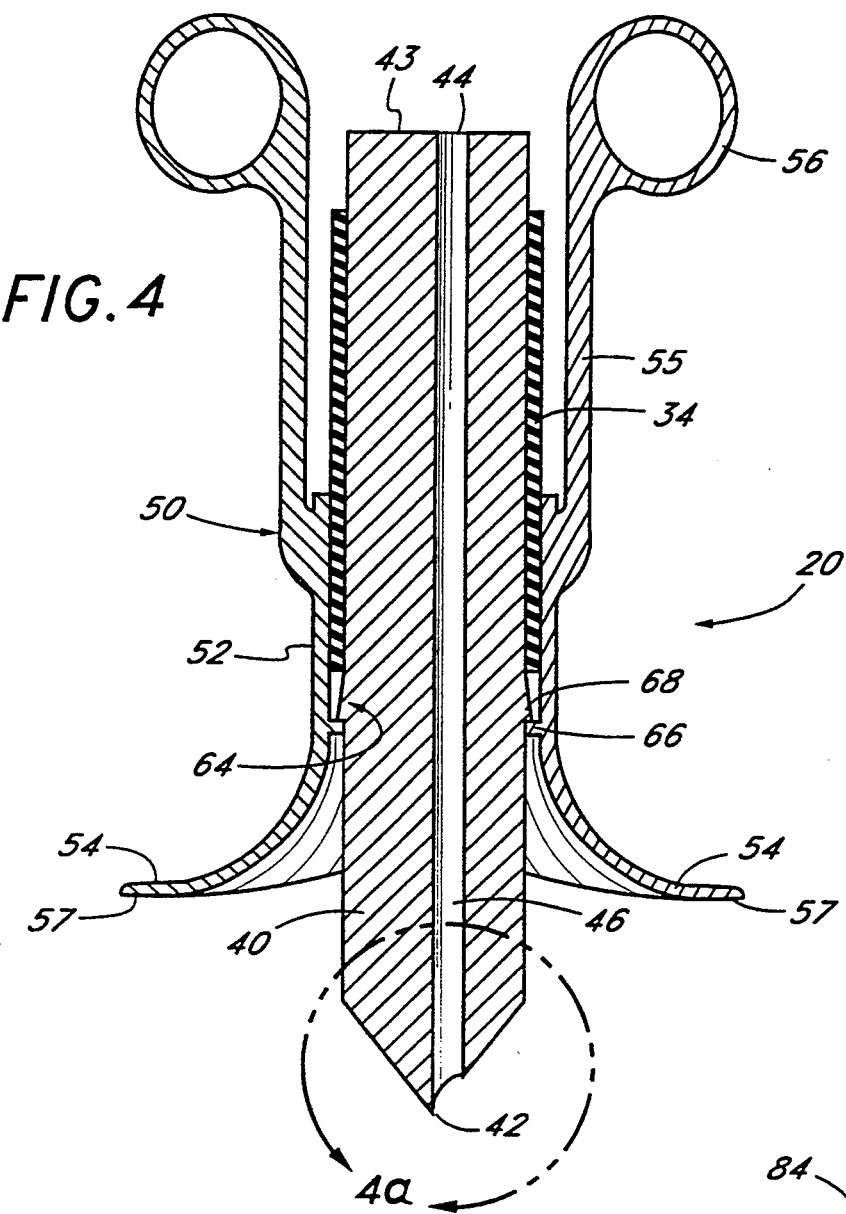
FIG. 4 is a cross-sectional view of one embodiment of a trocar of the present system in its assembled state, and further illustrates a trocal port formed in the trocar itself.

The trocar 40 is as described above and includes a raised circumferential ridge 68 near its distal end 42 which comprises a portion of a stop device 64, illustrated in more detail in FIG. 4. Shown at the top of the trocar 40 is the proximal opening 44 of the trocal port 46, which is a cylindrical passage shown in dotted lines extending longitudinally through the entire length of the trocar 40 and exiting on one face of the tip 42 of the trocar.

The retractor halves 51a,b are equipped with handles 55 having finger loops 56 for gripping and counter-traction, as explained above. When joined together, the two halves 51a,b comrise a guide portion 52 for receiving the trocar/cannula combination. The blades 54 extend approximately transversely to the axis of the trocar 40, and are insertable under the fascia 27 of the patient, as explained above in connection with FIG. 2. The retractor halves 51a,b are joined together by a latch mechanism 58 which is releasable and can also permit, if desired, the two halves to articulate with respect to one another. On the interior surface of the guide portion 52 of the guide halves 51a,b is shown an annular ledge 66 which interferes with the annular ridge 68 on the trocar 40 to provide a stop device 64.

If desired, blades 54 of this retractor 50 can be made shorter and smaller so as to not cause enlargement of the incision 22, thereby inhibiting the escape of carbon dioxide gas used for insufflation.

FIG. 4 illustrates in cross section the trocar system 20 of FIGS. 2–3. It will be noted that the trocar 40 in FIG. 4 is in the same position as illustrated in FIG. 2, with the trocar being inserted to its maximum extent and having penetrated the peritoneum 28. Thus, FIG. 4 illustrates the ridge 68 surrounding the trocar 40 resting against the interior ledge 66 of the retractor 50 in order to provide a stop device 64. This stop device 64, in combination with the counter-traction applied to the finger loops 56 of the retractor 50, provide an effective impediment to excessive travel and penetration of the trocar 40. In addition, FIG. 4 illustrates the cannula 34 surrounding the trocar 40 and inserted into the guide portion 52 of the retractor 50.

Figure 4A:
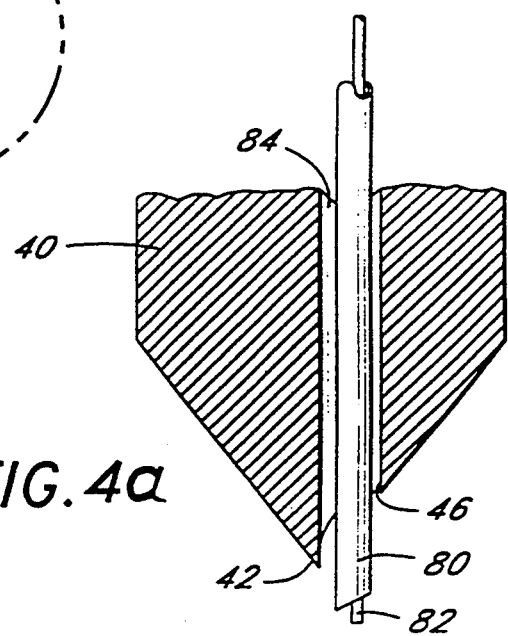
FIG. 4a is a detail view of the distal end of the trocar showing the trocal port and instruments therein.

FIG. 4 also illustrates the trocal port 46 which runs the length of the trocar 40 and allows the passage of endoscopic instruments. FIG. 4a is a close-up view of the distal opening of the trocal port 46 and illustrates a smaller auxiliary cannula 80 and interior endoscope 82 inserted therethrough. Thus, it will be noted from FIG. 4a that even with these instruments inserted in the trocal port 46, there is still an annulus 84 which allows the passage of insufflation gas. An important advantage of the present invention is that this trocar system 20 can eliminate the use of a verese needle (not shown) for insufflation purposes, which itself can be dangerous. In other words, the surgeon can inadvertently pierce or penetrate a vital organ 25 with the verese needle, thus causing injury to the patient. On the other hand, if the needle is not inserted deep enough, past the peritoneum, before insufflation begins, the state of pneumo-omentum occurs, which can also be injurious to the patient. With the trocar system 20 of the present invention, once the surgeon believes that penetration through the peritoneum 28 has been achieved, an auxiliary cannula 80 and endoscope 82 combination can be inserted through the trocal port 46 to visualize the extent of penetration of the trocar 40. If sufficient penetration has been achieved, initial insufflation can begin through the trocal port 46. Otherwise, continued trocar 40 penetration can be safely accomplished with visualization from the endoscope 82, as shown in FIG. 4a.

Another advantage realized by the trocal port 46 is the ability to insert and retract the trocar 40 from the endoscopic port 21 without forcing gas into the patient or suctioning matter from the patient. In other words, with a tight seal between a conventional solid trocar and cannula, the trocar acts substantially as a piston. The trocal port 46 of the present invention, however, provides a release means for any pressure differential between the body cavity and the exterior of the patient caused by trocar 40 movement.

FIGS. 5–10 illustrate the method of the present invention and the manner of using the trocar system 20 described above in connection with FIGS. 2–4.

Figure 5:
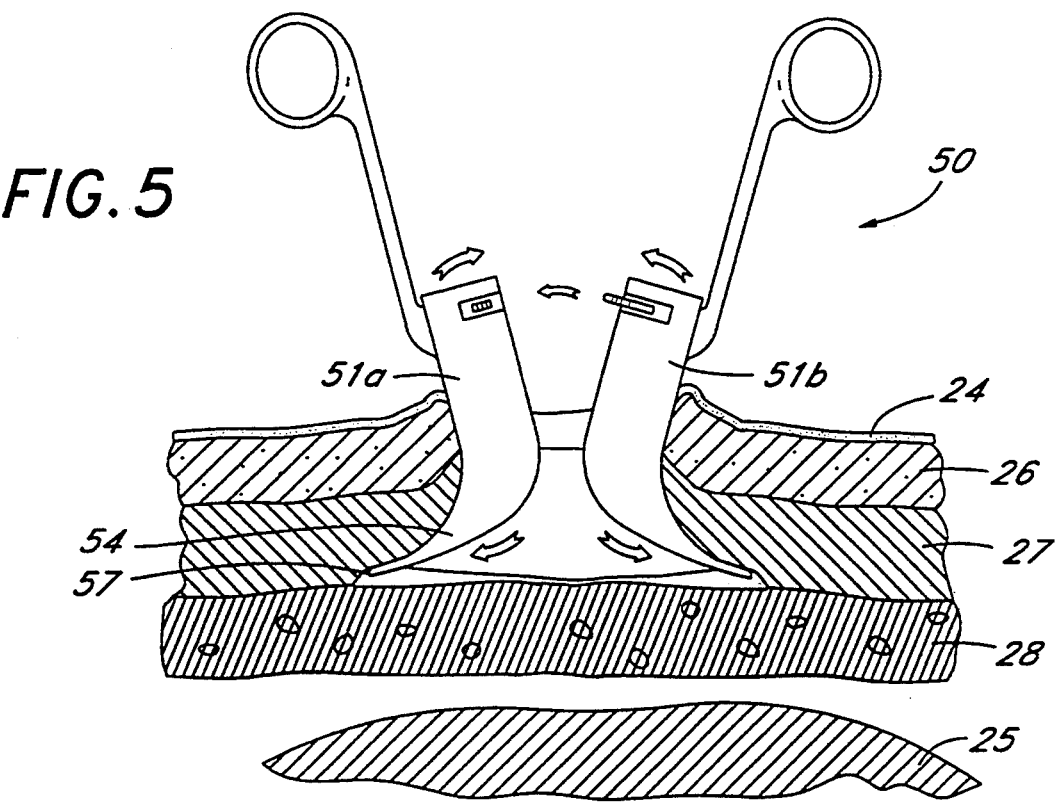
FIGS. 5–10 are partial cross-sectional views illustrating the method of the present invention, including the manner of its use.

FIG. 5 illustrates the manner in which the retractor 50 of the trocar system 20 is introduced into the patient. First, a deep incision 22 (FIG. 1) is made in the patient's skin 24 and fat layer 26 as the first step in the generation of an endoscopic port 21. This incision 22 comprises essentially a short stab incision which preferably reaches the deeper fascial tissue 27. If necessary, the walls of the incision 22 may be laterally retracted to aid in the insertion of the trocar system 20. One of the retractor halves 51a is then positioned near this incision 22 in a substantially horizontal manner such that the longitudinal axis of the retractor half is parallel to the patient's skin 24 at the location of the incision. In this configuration, the blade 54 of the retractor half 51a is substantially transverse to the patient's skin 24 and its distal end 57 is introduced into the incision 22 in a downward movement. The blade 54 of the retractor half 51a is inserted as deeply as necessary into the incision 22. The retractor half 51a is then rotated approximately 90° in a clockwise direction, as indicated by the arrows in the left-hand side of FIG. 5. This rotation brings the retractor half 51a into a position which is essentially perpendicular to the patient's skin 24 at the location of the incision 22 and causes the tip 57 of the blade 54 to penetrate laterally and beneath the fascia 27 until an erect position is assumed, as shown in FIG. 6.

A similar motion is performed with respect to the opposite retractor half 51b except that the rotation is counter-clockwise, as shown by the arrows on the right side of FIG. 5. When both retractor halves 51a,b are brought to an erect position, they may be brought together in the direction of the arrows shown in FIG. 6 and interconnected by means of the latch 58.

Figure 7:
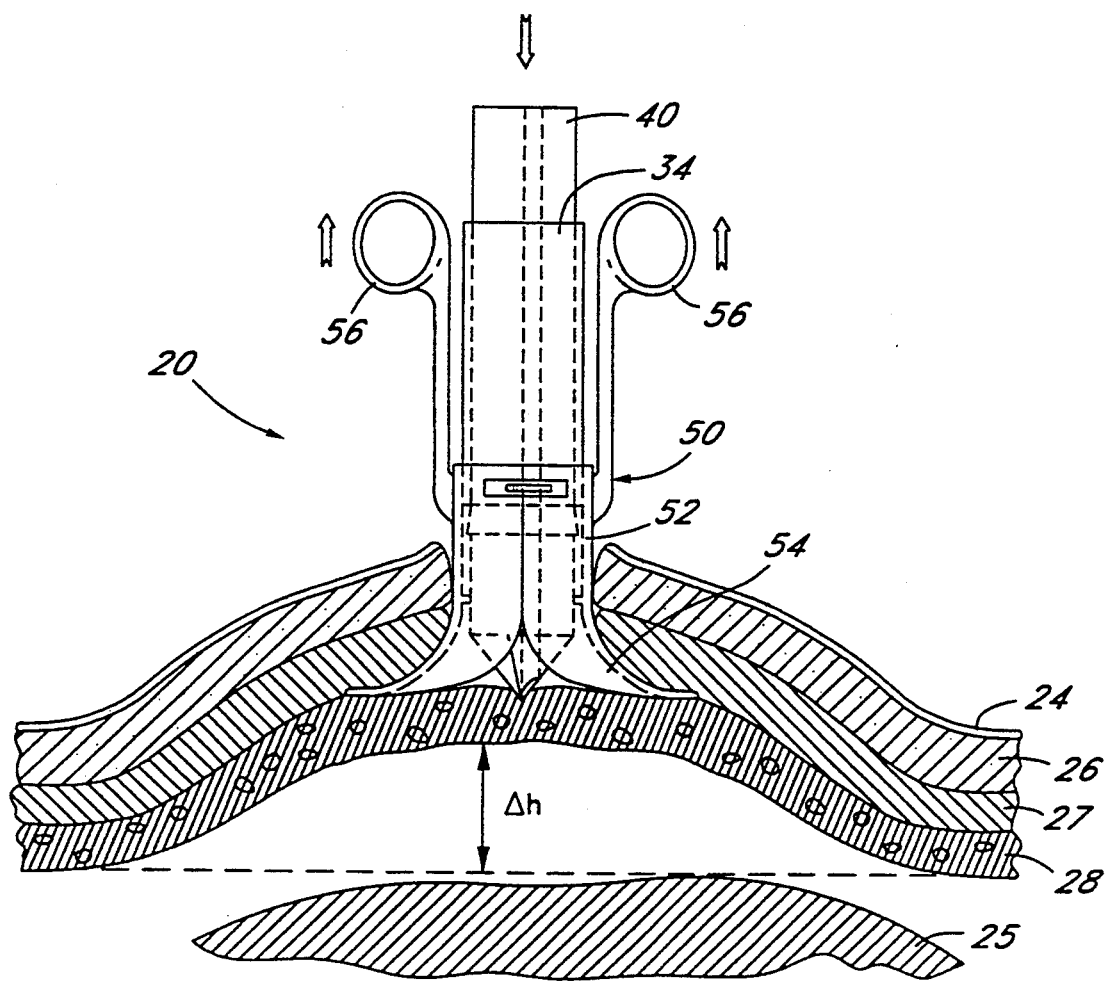

The advantage of this method of insertion of the retractor halves 51a,b is that it minimizes the size necessary for the incision 22 and maintains a smaller incision opening during installation. Moreover, the blades 54 of the retractor 50 are inserted securely beneath the fascia 27 in accordance with this method. Therefore, improved counter-traction can be obtained by the blades 54, as explained above in more detail. With the retractor halves 51a,b secured together as shown in FIG. 7, they provide a secure and erect guide portion 52 for the trocar/cannula combination to be inserted therethrough, the retractor 50 is self-supporting and can hold other instruments, including the cannula 34 and the trocar 40 without having to be supported by the surgeon's hands. This allows the surgeon to accomplish other procedures, thereby shortening the time for this endoscopic port procedure.

Figure 6:
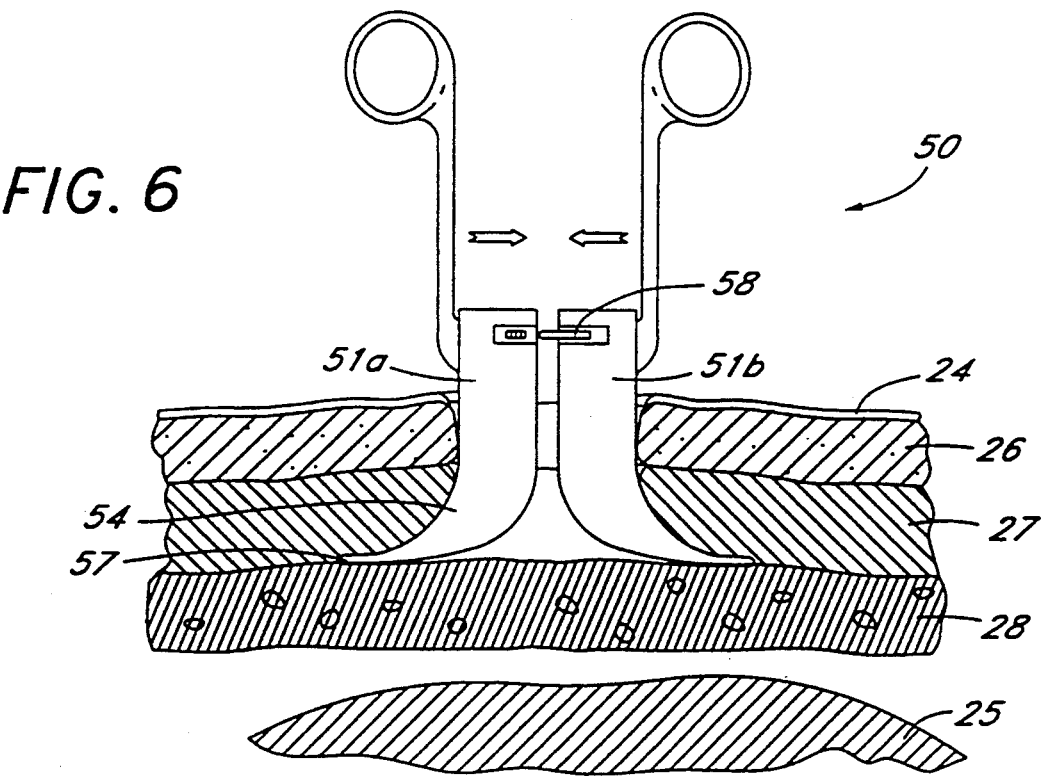
Figure 8:
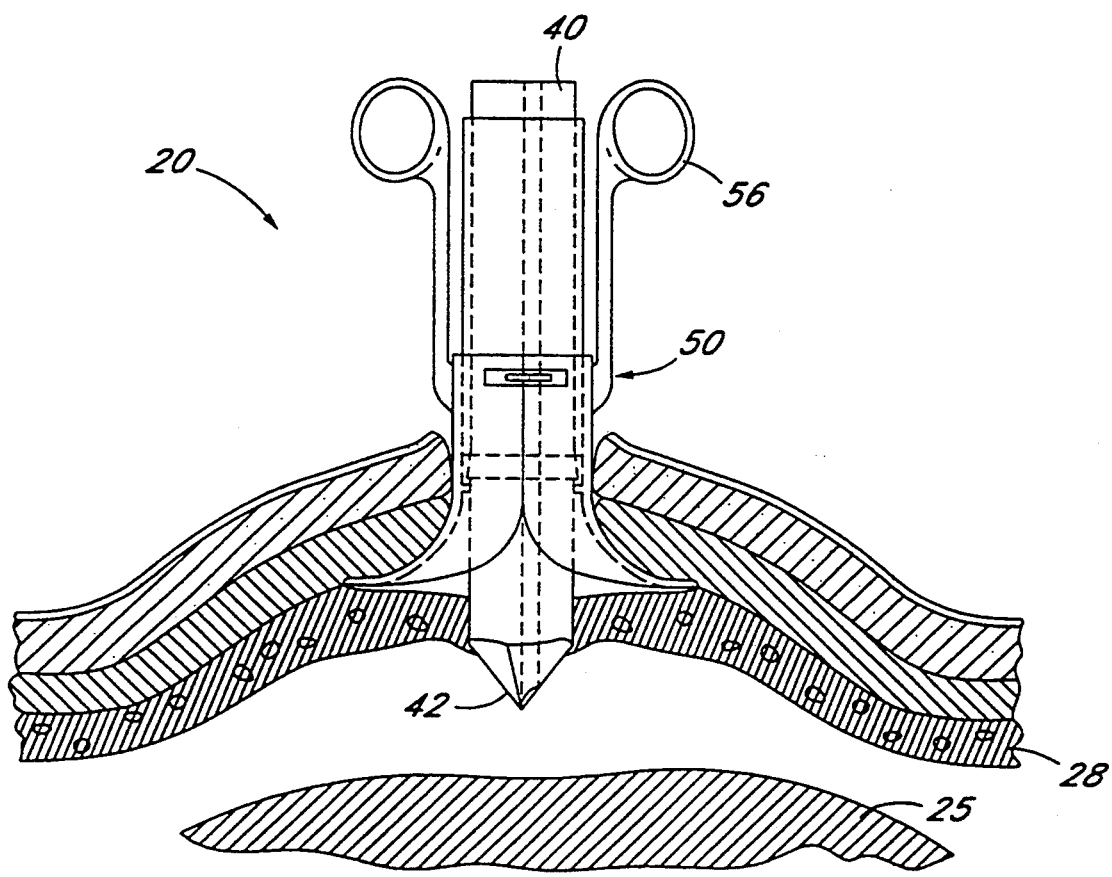

It will be noted in FIGS. 5 and 6, the close proximity of the vital organs 25 just beneath the peritoneum 28. FIG. 7 illustrates, in a manner similar to FIG. 2, the use of the present invention to retract the peritoneum 28 and other tissue layers upwardly away from the vital organs 25 prior to the penetration of the trocar 40. Thus, it will be noted that once the trocar 40 and cannula 34 are inserted into the retractor 50, a retraction of approximately $\Delta h$ can be achieved in accordance with the device and method described above. Once this retraction has been achieved, penetration of the trocar 40 can safely begin. The counter-traction, as achieved by the handle finger loops 56 and manual force applied thereto in the direction of the arrows shown in FIG. 7, tends to neutralize the downward momentum of the trocar's penetration, thus further insulating the vital organs 25 from injury. Finally, as shown in FIG. 8, once the trocar 40 has completely penetrated the peritoneum 28, forward progress of the trocar 40 is easy to control due to the effect of counter-traction and the tension placed upon the peritoneum 28 at the point of penetration by the counter-traction itself. If it is desirable and necessary to continue penetration of the trocar 40, that can be safely accomplished with the assistance of endoscopic visualization in the manner described above in connection with FIG. 4a.

Figure 9:
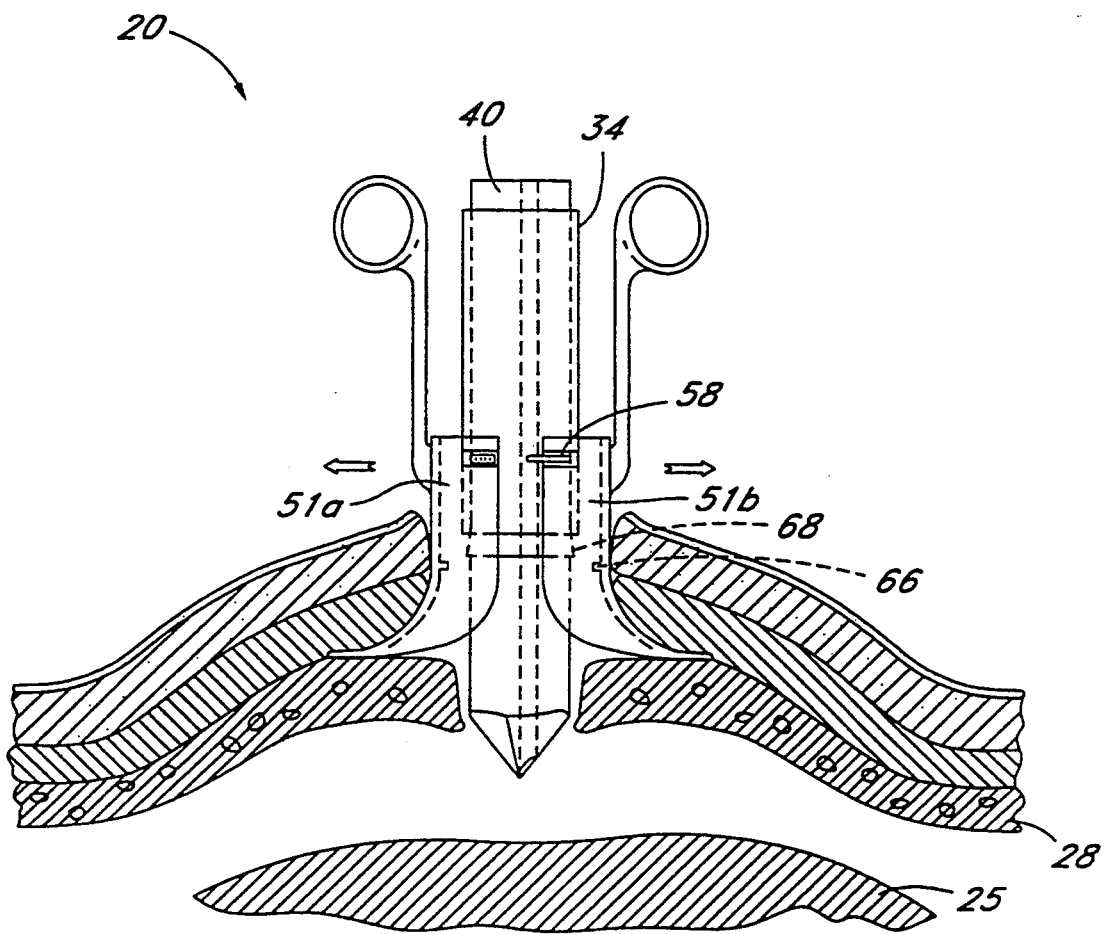
Figure 10:
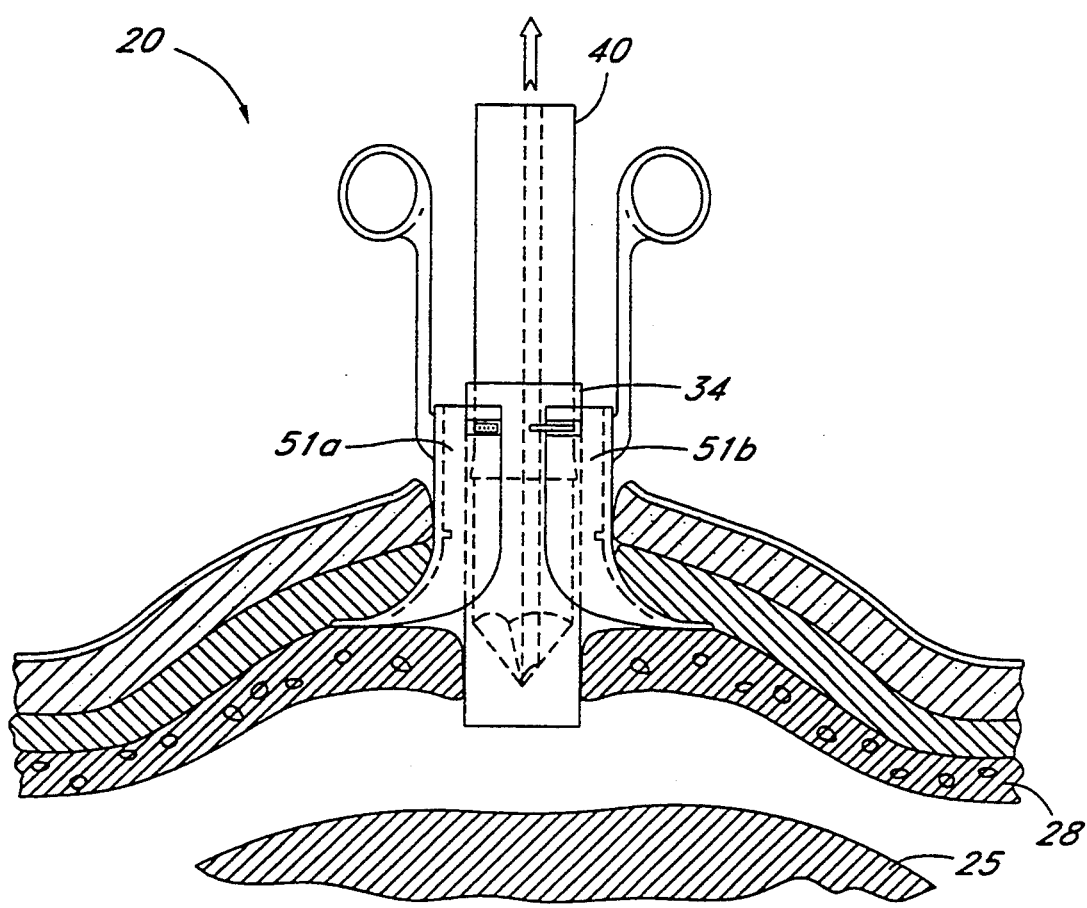

FIGS. 9 and 10 illustrate the manner in which the cannula 34 of the present trocar system 20 can be installed in place in order to form the endoscopic port 21. The retractor halves 51a,b of the trocar system 20 are first separated slightly, in a manner similar to FIG. 6, by disconnecting the latch 58. This slight separation allows the cannula 34 to pass downward over the ridge 68 on the trocar 40 and past the interior ledge 66 of the retractor halves 51a,b. Thus, the cannula 34 can be advanced downward through the hole in the peritoneum 28 formed by the trocar 40, using the trocar as a guide. Once the cannula 34 is in place through the peritoneum 28, as shown in FIG. 10, the trocar 40 can be removed so as to allow the passage of endoscopic instrumentation. If desired, the retractor halves 51a,b can be once again connected to provide a rigid vertical support for the cannula 34 or for other instruments that may be placed therethrough.

Trocar System of FIGS. 11–16

Figure 11:
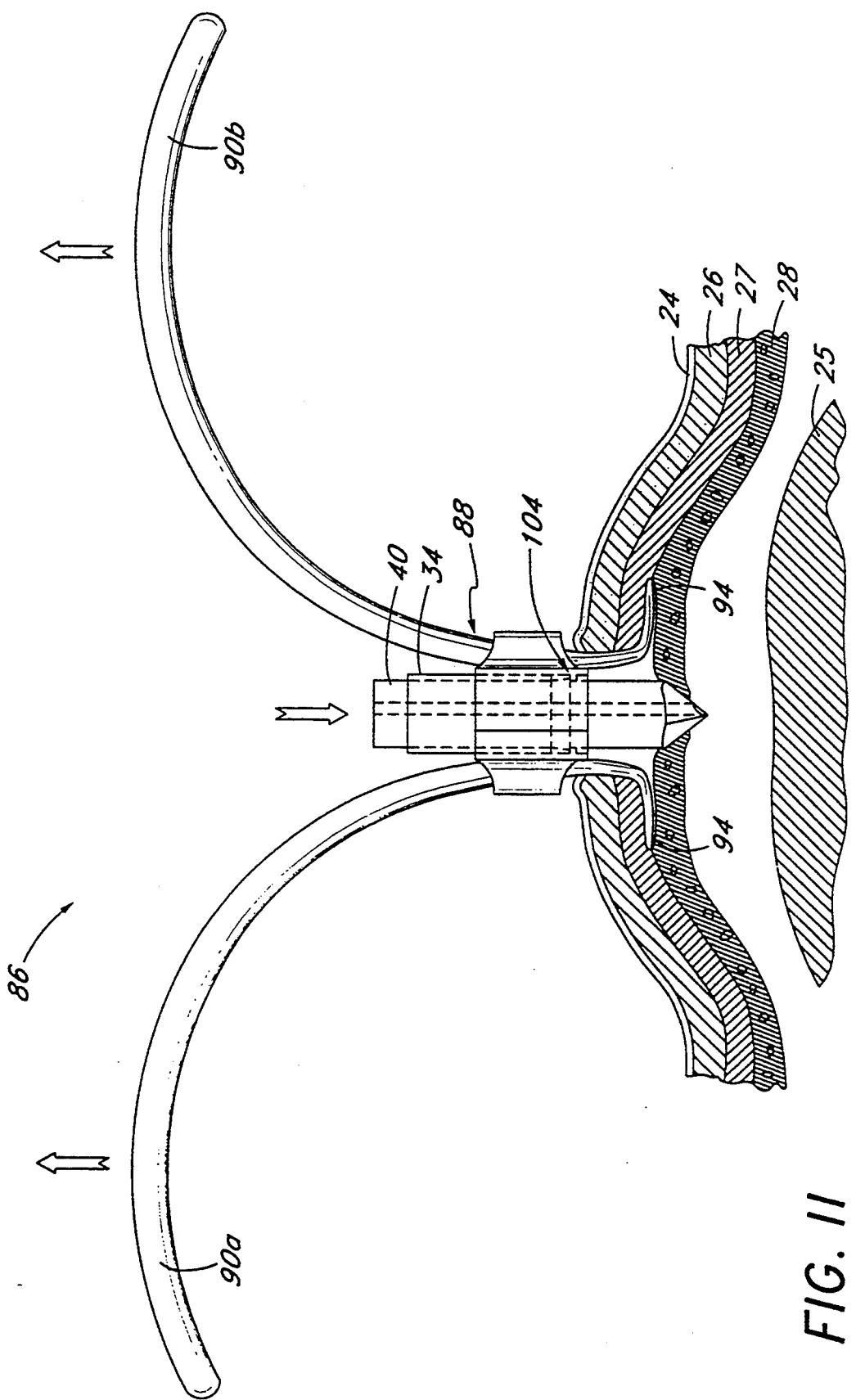
FIG. 11 is a partial cross-sectional view illustrating another embodiment of the trocar system of the present invention using larger handles for counter-traction which are suitable for two-handed use.

FIG. 11 illustrates another embodiment of trocar system 86 of the present invention in which the trocar retractor 88 is provided with large arcuate handles 90a,b, the distal ends of which form the blades 94 for insertion under the fascia 27. With this retractor 88 configuration, greater counter-traction can be achieved because the lifting force, as shown by the arrows in FIG. 11, is applied directly to the blades 94 and to the fascia 27. If desired, retraction in the reverse direction can be achieved with both hands of the surgeon while trocar penetration is achieved with one of the thumbs. If desirable, or necessary, an assisting surgeon may retract the handles 90a,b while the head surgeon manipulates the trocar 40 down into the peritoneum 28. Thus, the trocar 40 and cannula 34 are utilized in connection with the retractor 88 of FIG. 11 in a manner similar to that as described above for the trocar system 20 of FIGS. 2-10.

It will be noted that the blades 94 formed on the end of the retractor handles 90a,b are somewhat shorter and more angular than the blades 54 of the previous embodiment. This configuration allows for a more secure grip by the blades 94 and handles 90a,b beneath the deep fascial layer 27 in order to improve counter-traction. This is an important advantage since, in some patients, the layer of subcutaneous fat 26 can measure up to 10-20 centimeters.

The two halves 96a,b which form the trocar guide 98 of this embodiment are also configured somewhat differently, as illustrated in detail in FIGS. 12-16. In this embodiment, each guide half 96a,b is slidably mounted on its respective handle 90a,b by means of a channel 100. Thus, either guide half 96a,b can be slid up and away from the incision site during installation of the trocar system 86. Specifically, FIGS. 12-15 illustrate the method associated with the present invention and the manner of use of this particular retractor 88 within the trocar system 86.

Figure 12:
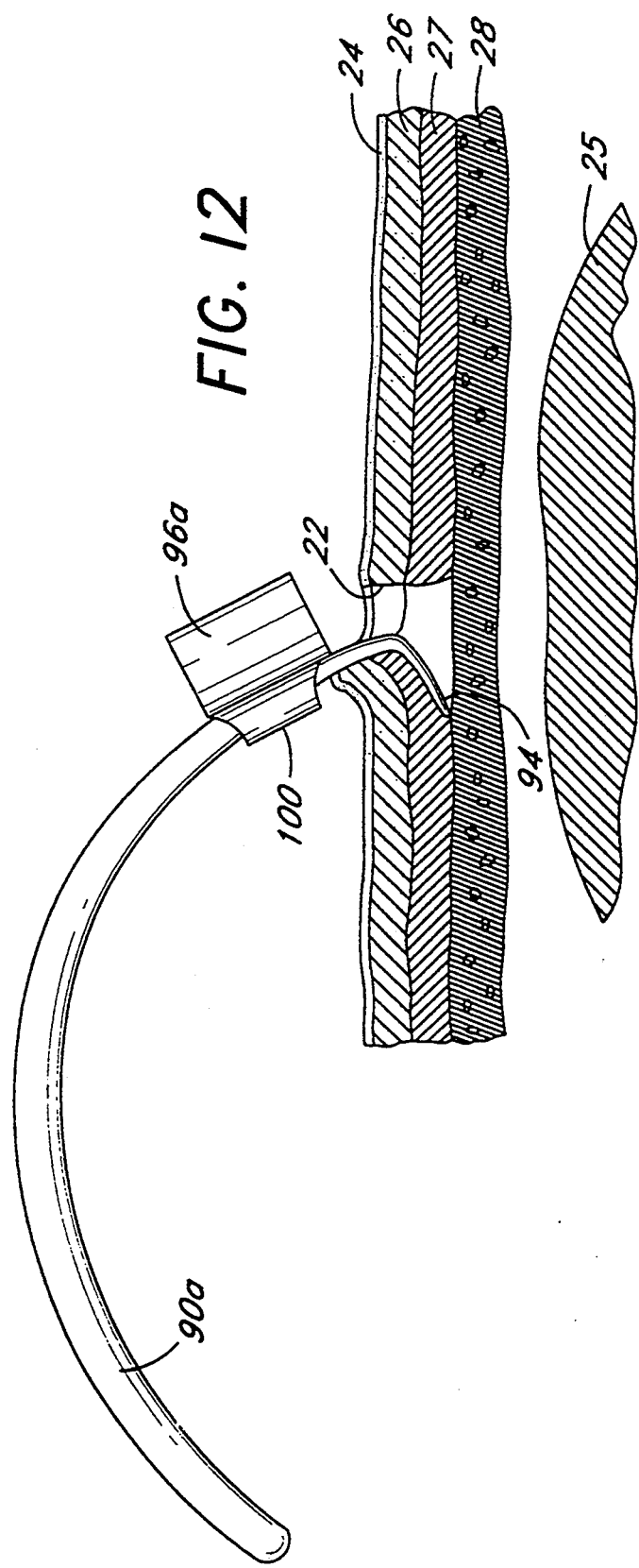
FIGS. 12–15 illustrate the manner and method of using the trocar of the second embodiment of the present invention.
Figure 13:
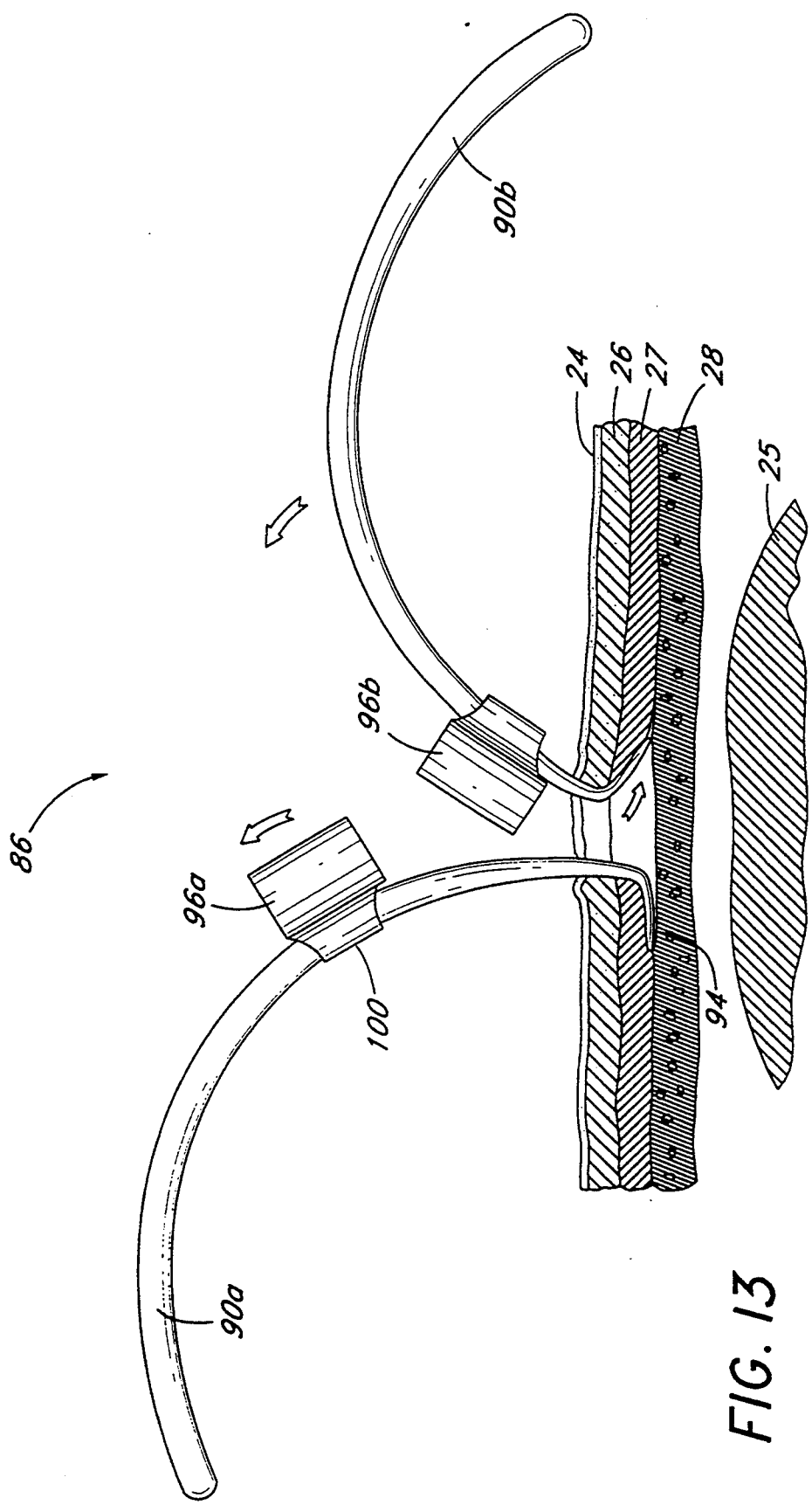

Referring to FIG. 12, the first incision 22 causes some relaxation of the skin 24, fat 26, and fascial layer 27, causing them to part slightly. However, if necessary, the incision 22 can be retracted slightly in a lateral direction in order to facilitate introduction of the trocar system 86. In a manner similar to that described above in connection with the trocar system 20 of FIGS. 2-10, the blade 94 of one of the handles 90a of the trocar retractor 88 of FIG. 12 is introduced into the incision 22 in a direction substantially transverse to the patient's skin 24. The handle 90a is then rotated approximately 90° in a clockwise direction such that the retractor blade 94 assumes the position shown in FIG. 13. Thus, the blade 94 is inserted beneath the fascial layer 27 for secure counter-traction. It will also be noted from FIG. 13 that the associated guide half 96a can be slid upward so as to not interfere with the installation of the guide half 96b on the opposite handle 90b. The second handle 90b is installed in a similar manner except that rotation is in a counter-clockwise direction, as shown by the arrow in FIG. 13.

Figure 14:
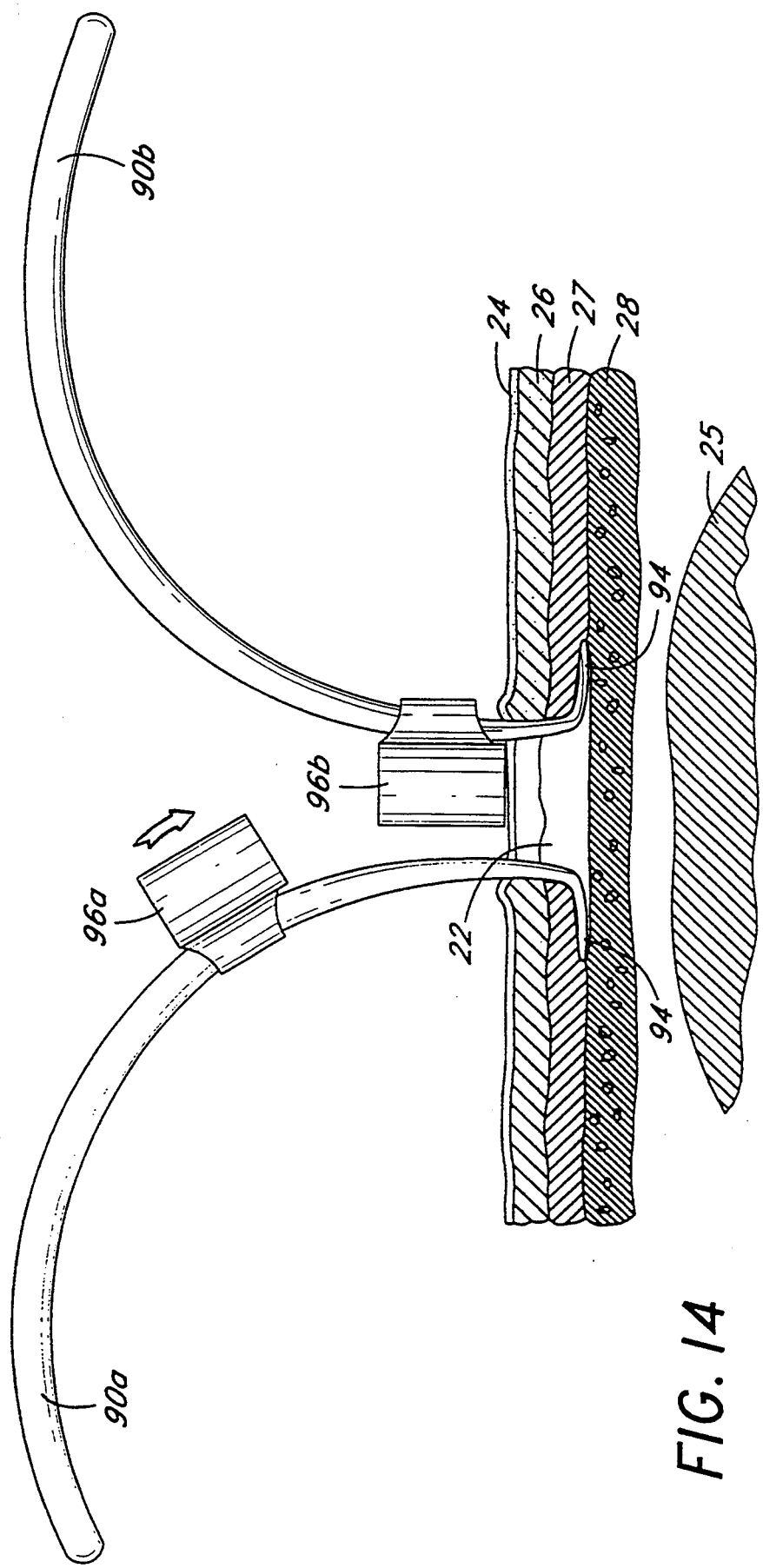
Figure 15:
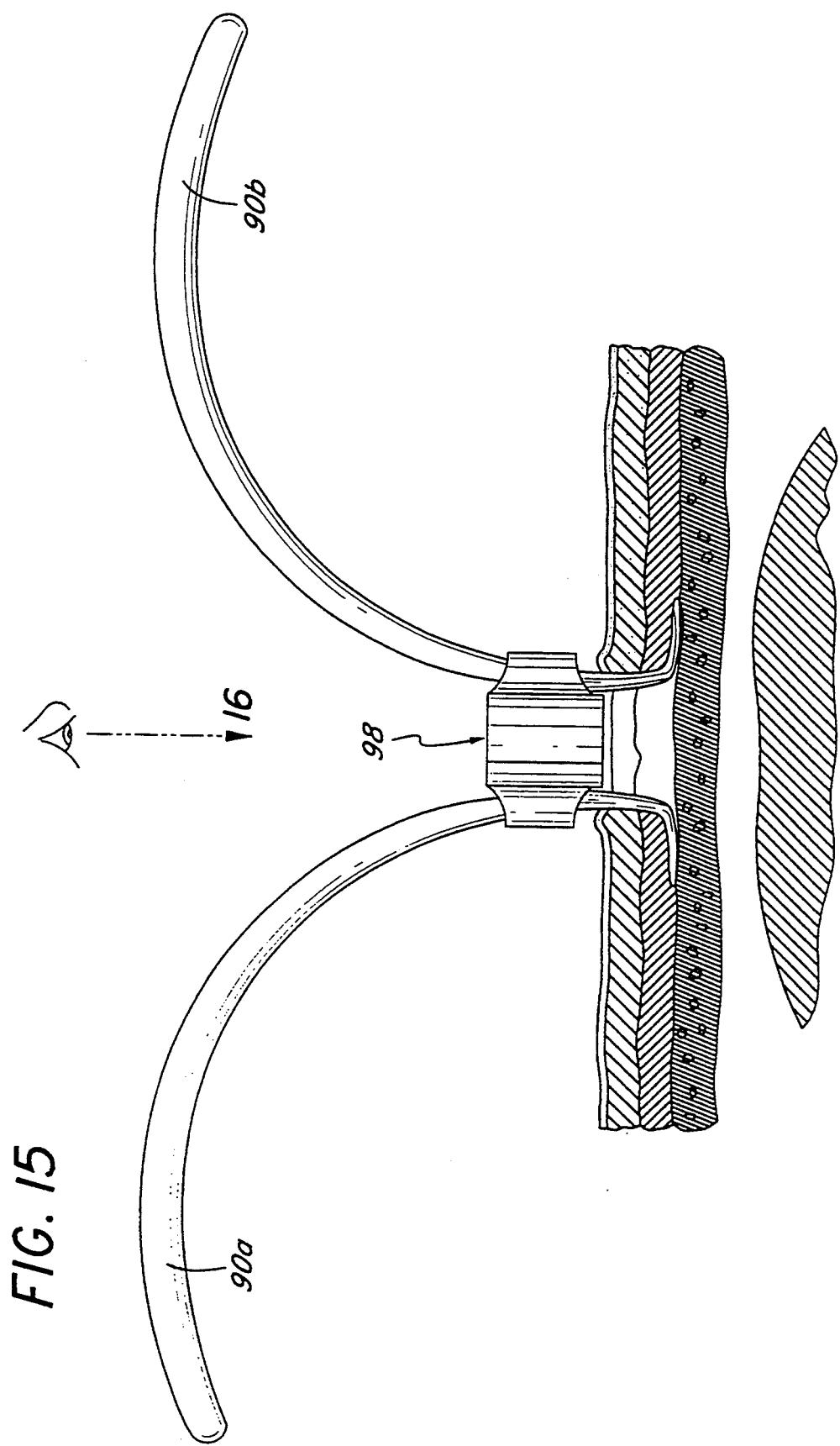

FIG. 14 illustrates the positions of the handles 90a,b once they are installed in the incision 22. The first guide half 96a can then be slid downwardly into a nesting, mating relationship with the second guide half 96b to form a complete cylindrical guide 98, as shown in FIG. 15. The completed guide 98 can then receive the trocar/cannula combination, as illustrated in FIG. 11.

Figure 16:
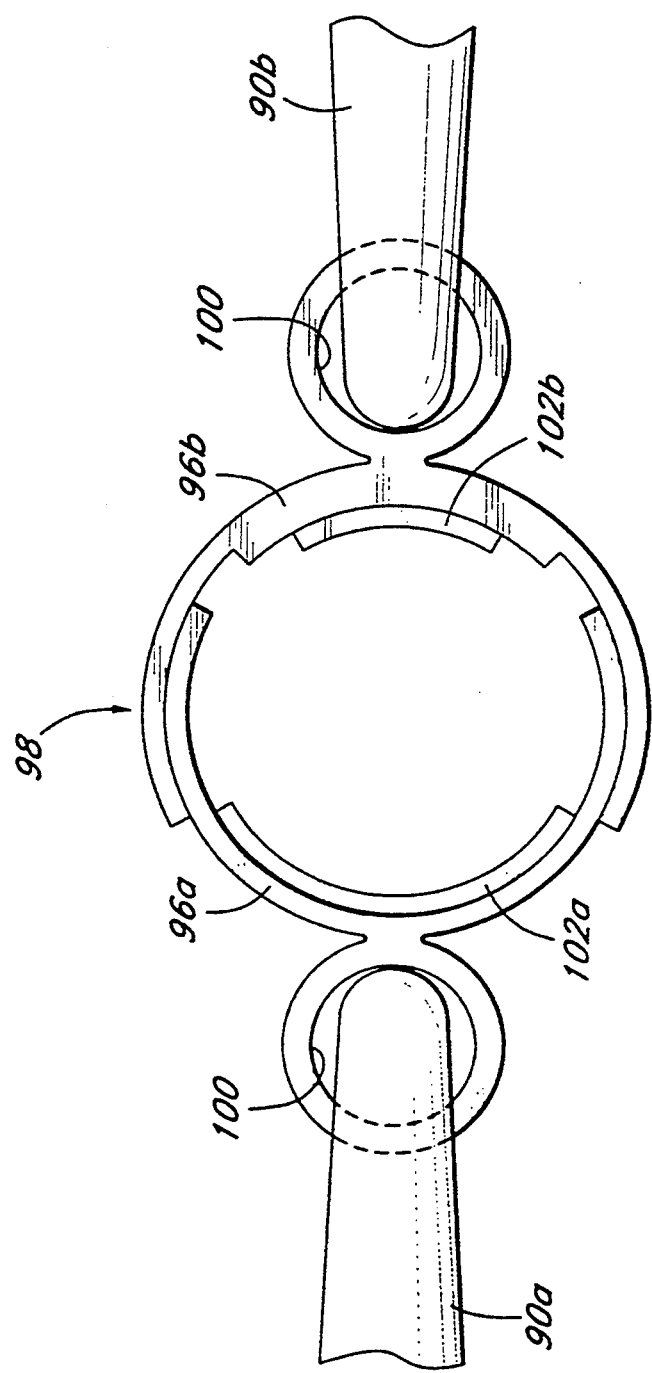
FIG. 16 is a top view of the second embodiment of the trocar of FIGS. 11–15.

FIG. 16 illustrates a top view of the present trocar system 86, including the completed guide 98 and the overlapping ends of each respective guide half 96a,b. Also illustrated are interior ledges 102a,b combining to act as a trocar stop device 104 (seen in FIG. 11), in a similar manner to the embodiment shown in FIGS. 2-10. Mounted on the exterior of the guide halves 96a,b are the channels 100 which slidably receive the respective guide handles 90a,b, as explained above.

Thus, the trocar system 86 of this embodiment can be efficiently utilized to maximize counter-traction.

Trocar System of FIGS. 17-21

In some cases, the trocar systems 20, 86 of the previous embodiments may not provide a sufficient engagement between the blades of the trocar retractor to achieve the degree of retraction or counter-traction necessary. For example, the fat layer 26 of the patient may obscure the visualization of the fascia 27 deep in the incision 22 and prevent the correct placement of the blades of the trocar guide. In addition, in order to avoid the loss of insufflation gas around the site of retractor insertion, it may be desirable to use a blade configuration which will not tend to enlarge the incision 22 to any degree beyond only that which is necessary to form the endoscopic port.

Figure 17:
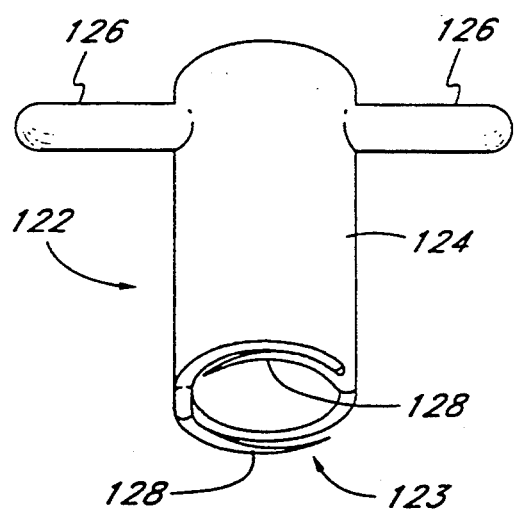
FIG. 17 is a perspective view of a retractor of yet another embodiment of the present invention having distal teeth for securely gripping the fascial tissue.

Accordingly, the trocar system 120 of another embodiment is illustrated in FIGS. 17-21. Referring first to FIG. 17, there is shown the trocar retractor 122 of this embodiment which comprises a complete cylinder, or guide portion 124, having a pair of opposed transverse handles 126 for providing counter-traction. At the distal end 123 of the retractor 122, there is shown a pair of sharp pointed teeth grippers 128 constructed in rotary or corkscrew fashion. As will become apparent below, these grippers 128 are designed to bore into the fascial tissue 27 in order to provide a secure gripping force for the retractor 122. In this manner, sufficient counter-traction force can be applied to the incision site without excessive enlargement of the incision 22 and without the need for deep fascial visualization.

Figure 18:
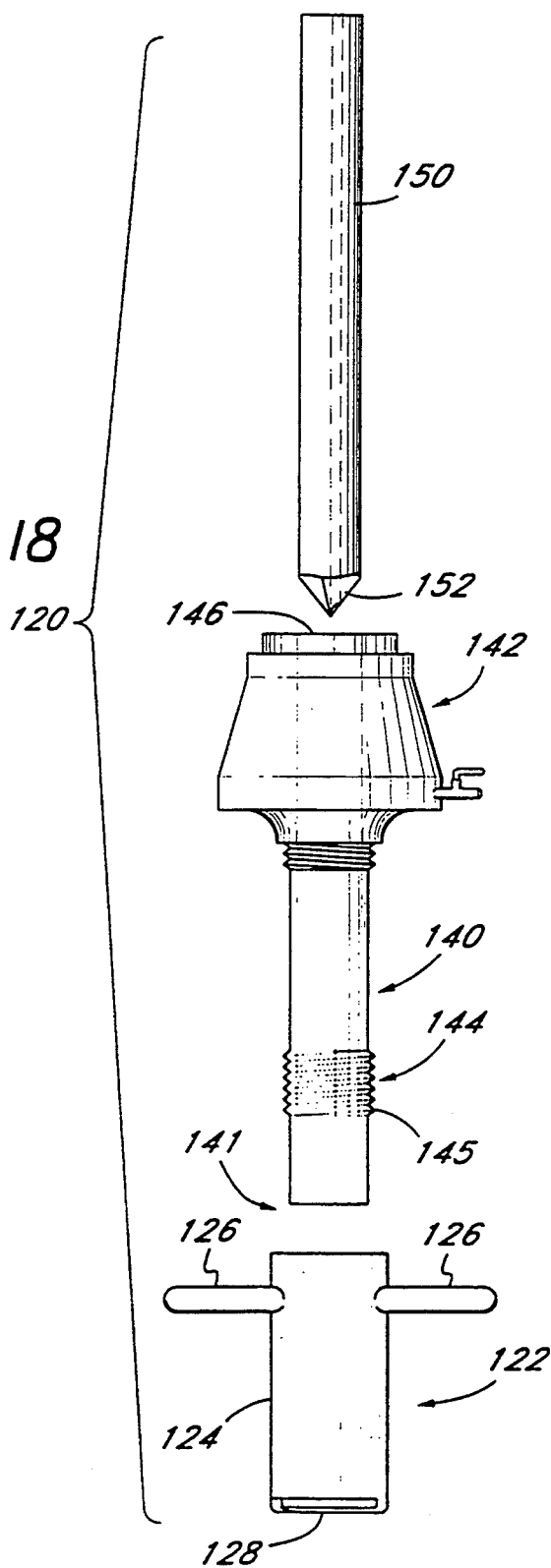
FIG. 18 is an elevational view of the retractor of FIG. 18 in the trocar system including a trocar, cannula, cannula head piece and rotary seal.

FIG. 18 illustrates the complete trocar system 120 of this embodiment, including the retractor 122 described above, the cannula 140 including its associated integral head piece 142 at the proximal end, and the trocar 150 extending through the cannula. Also shown near the distal end 141 of the cannula 140 is a rotary seal 144 having exterior threads 145 which prevents the loss of insufflation gas around the cannula 140 at the site of penetration.

In somewhat conventional fashion, as shown in FIG. 18, the head piece 142 contains a flapper valve 146 for preventing the loss of insufflation gas. However, this valve 146 allows for the passage of the trocar 150 down through the head piece 142 and the cannula 140, such that the tip 152 of the trocar 150 is exposed at the distal end 141 of the cannula 140. Thus, once the trocar 150 has penetrated the peritoneum 28 in order to form the endoscopic port, the trocar can be removed, leaving the cannula 140 and head piece 142 in place. The valve 146 prevents the loss of insufflation gas but allows the passage of other endoscopic instruments therethrough. The method of this invention and the manner of use of the trocar system 120 of this embodiment is illustrated in connection with FIGS. 19 and 20.

Figure 19:
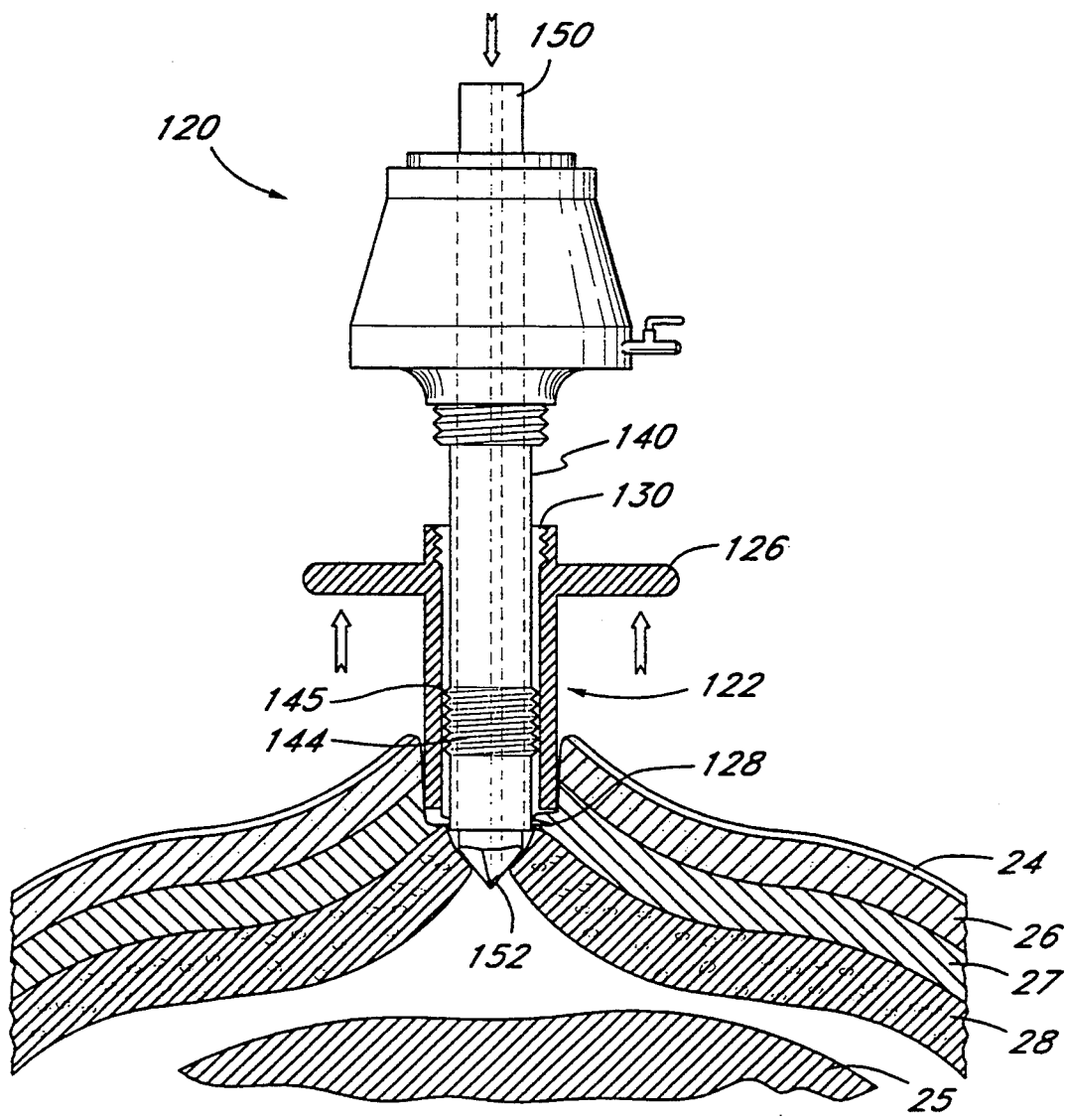
FIGS. 19–21 illustrate the manner and method of using the trocar of the third embodiment of the present invention.

Referring first to FIG. 19, after the incision 22 is made, the retractor 122 alone is inserted into the incision 22 in order to initiate the counter-traction process. Typically, retraction of the incision 22 is not necessary to allow introduction of the retractor 122; however, if desired, slight retraction of the incision can be accomplished in order to facilitate the passage of the retractor into the deeper facial tissues 27. An important advantage of the trocar system 120 of this embodiment, however, is the fact that actual visualization of the facial tissues 27 is not necessary. Once the retractor 122 has been securely seated in the incision 22, it can simply be rotated by means of the handles 126 approximately one-quarter or one-half turn in order to cause the rotary grippers 128 to bite or securely grip the deep fascial tissues 27 in the incision. Thus, as shown in FIG. 19, counter-traction can then be applied to the handles 126 in order to lift the tissue layers of the patient away from the vital organs 25 beneath. At the same time, the cannula 140 and trocar 150 combination can be passed down through the retractor 122, in the same manner as explained above, and penetration of the trocar through the peritoneum 28 can be accomplished. In this embodiment, the rotary seal 144 provides a form of a stop device because of the threads 145 located on the exterior thereof. In other words, the threads 145 interfere with the tissues on the side walls of the incision 22 and provide a resistance to deeper penetration. This advantage, combined with effective countertraction, protects the vital organs 25 beneath the tip 152 of the trocar 150.

Figure 20:
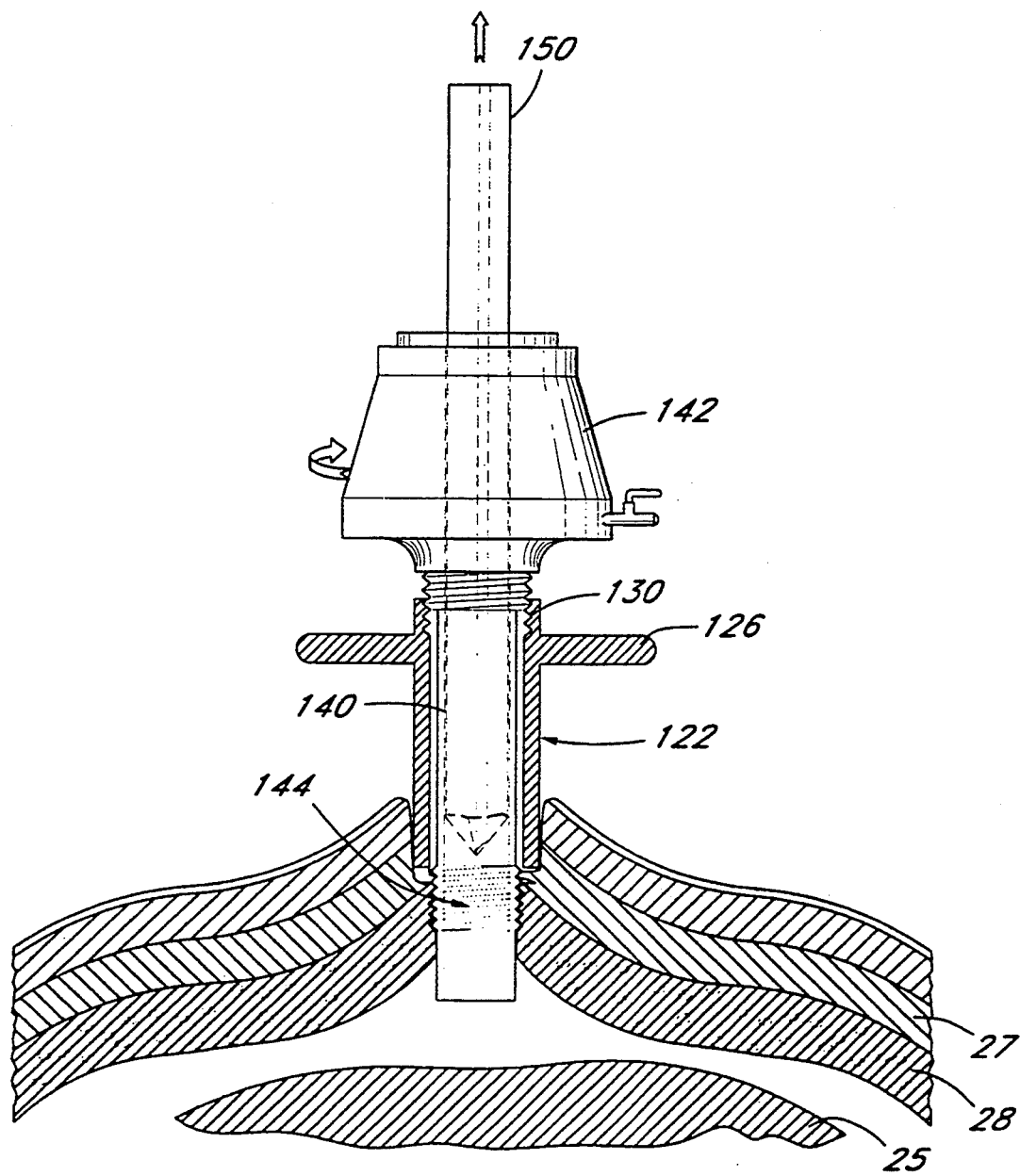

After penetration is achieved, and the trocar 150 is removed, the seal device 144 can be rotated downwardly into place, as shown in FIG. 20, so as to provide an effective seal against the loss of insufflation gas. Rotation of the head piece 142 and cannula 140 will effectively impart rotation to the seal 144 and cause it to advance downward and secure the grip of the walls of the incision 22. Rotation continues until the seal 144 is located at the proper depth, which varies depending on the abundance of fat tissue or lack thereof.

It should be noted that the seal 144 assumes only a frictional fit along the shaft of the cannula 140 so as to be positioned at the appropriate depth for placement in the incision 22. Thus, the length or thickness of the seal 144 can be modified and adjusted on a patient by patient basis depending upon the thickness of the tissue layers of the patient and the degree of seal desired. Therefor, the surgeon may make last minute adjustments to ensure the endoscopic port is complete and ready for use, as illustrated in FIG. 20.

It should also be noted that the head piece 142 of the cannula 140 can be threaded into threads 130 in the proximal portion of the retractor 122 after location of the seal 144 in order to provide a secure mounting for the head piece 142. Other securing means such as cooperating sliding members adapted to be locked are contemplated. In addition, the secure gripping of the retractor 122 of this embodiment is such that in many cases it will support itself rigidly or upright in the incision 22, thereby freeing up the hands of the surgeon to perform other procedures. Thus, other endoscopic instruments and the like can be supported in the port without auxiliary ports or manual assistance from the surgeon. In addition, other instruments with adapted screw tips can be threaded into the proximal threaded portion 130 of the retractor 122.

Figure 21:
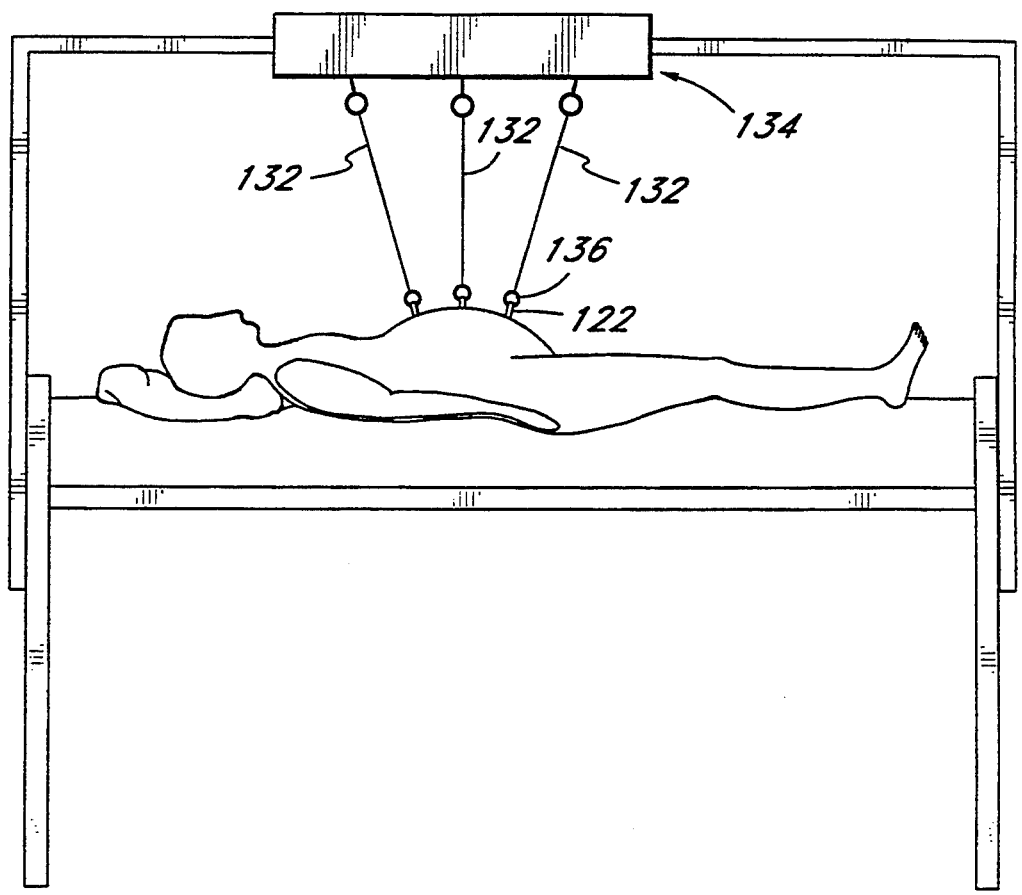

The retractor 122 of this embodiment, with its oblique gripping action on the fascial tissues 27 of the patient, is sufficiently efficient to eliminate the use of pneumoperitoneum altogether. Thus, as shown in FIG. 21, with the use of several retractors 122 of this embodiment, the outer tissues of the patient can literally be lifted away from the vital organs 25 and secured by wires 132 to a scaffolding or support mechanism 134, thus avoiding the use of insufflation gas. The placement and number of the retractors 122, of course, will depend upon the type of endoscopic surgery being conducted. The method for securing the retractors 122 is the same as explained above in the context of FIGS. 17–20. Also, appropriate rings or loop devices 136 or other tie-down devices can be applied to the retractors 122 in order to facilitate securing them to the surrounding support structure.

Figure 22:
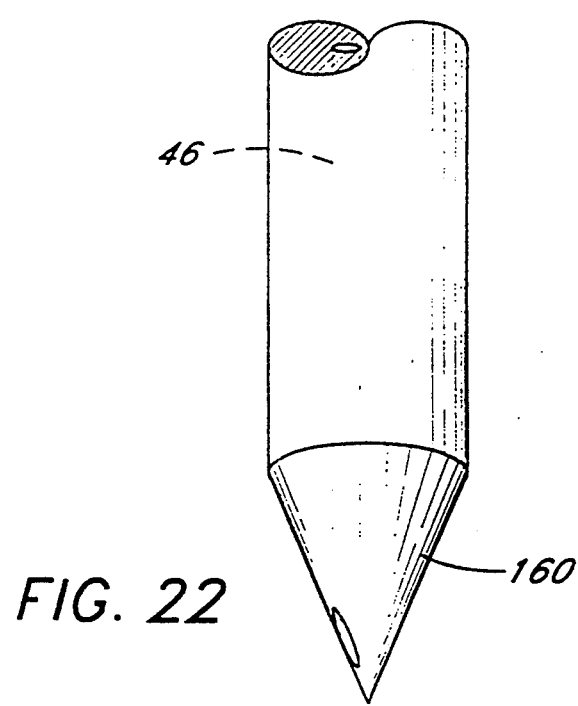
FIG. 22 illustrates an improved trocar tip for use with the trocar system of the present invention.

Trocar of FIG. 22

The present invention also contemplates an improved trocar tip for use in connection with the trocar system of the present invention. Such a trocar tip is illustrated in FIG. 22 and described below in more detail.

It will be noted that in a conventional trocar, the tip is essentially pyramidal, being comprised of three sides or faces, each separated by a sharp edge. Conventional trocar tips are configured in this manner because they cut in three directions along the blade faces, thereby facilitating the ability of the trocar to penetrate the strong, elastic peritoneum. That is, since a substantial amount of force is necessary to pierce the peritoneum, it is understood that this conventional trocar tip will penetrate much more quickly. Surgeons using this tip rely substantially on the momentum that is generated in the hand penetration motion to produce penetration.

However, conventional trocar tips suffer from important disadvantages which are well understandable. First, the blade faces obviously cut the tissues in three directions, generating a larger hole and causing substantial lacerations in the patient's tissues. Although this is a serious disadvantage, it is tolerated because of the need to penetrate the peritoneum as explained above. However, if the opening left by the trocar penetration is not adequately repaired, a herniation at that location may occur or other adhesions may cause substantial pain and discomfort to the patient. An adhesion occurs where the lining of the peritoneum is not smooth, as with scar tissue. Thus, an intestine or other tissue adheres to the peritoneal cavity at the point of trocar penetration and prevents independent movement of the peritoneum separate and apart from that organ.

With the trocar system of the present invention, the need to use an extremely sharp three-sided trocar tip is eliminated. In other words, because of the control provided by the present trocar system, including the use of counter-traction which places the peritoneum in tension to facilitate penetration, a less damaging trocar can be utilized. Thus, as shown in FIG. 22, a conical trocar tip 160 is illustrated which is suitable for use with the trocar system of the present invention.

Since the surgeon need not depend on the momentum of penetration, but can achieve good manual control of the trocar without injury to the internal organs, only a small opening in the peritoneum is created by the trocar tip. Thereafter, possibly with the aid of endoscopic visualization through the trocal port 46 as explained above in more detail, the trocar 160 can be advanced to the degree necessary to generate the endoscopic port. In this manner, the tissues experience less laceration and only a round or circular opening or wound is experienced. This type of wound is much easier to close, thereby reducing the risks associated with adhesions and hernia. In other words, after the initial hole in the peritoneum is formed, the hole is expanded rather than being cut or shredded as with the conventional trocar tip.

Although this invention has been described in terms of certain preferred embodiments, it is intended that the scope of the invention not be limited to the specific embodiments set forth herein. Accordingly, the scope

What is claimed is:

1. A trocar system for assisting in the establishment of a port in a patient's body for endoscopic surgery, comprising:

a trocar for penetrating the exterior tissues and peritoneum of said patient to produce a hole therethrough;

a cannula for surrounding said trocar and forming said port in said hole upon removal of said trocar;

a retractor for gripping the exterior tissues of said patient to allow said tissues to be lifted away from vital organs thereof, whereby the penetration of said trocar can be better controlled so as to avoid accidental injury to said vital organs;

said retractor comprising a hollow, cylindrical guide portion for receiving said cannula and said trocar and for guiding the direction of penetration of said trocar, said guide portion being slidable with respect to said cannula and said trocar, and having a distal end;

at least one handle to allow a counter-traction force to be applied to said retractor in a direction substantially opposite to the penetration of said trocar, prior to penetration by said trocar, and a leading edge comprising a pair of rotary blades extending distally past the terminal, distal end of the guide portion, each of said blades having an exposed sharp distal tip and a proximal end, each of said blades being mounted on said guide portion solely at said proximal end and being exposed along its entire length from said proximal end to said distal tip in order to permit said blade to pass though a perforation in said exterior tissues formed by said sharp distal tip, whereby said blades can remain imbedded in said exterior tissues for more efficient retraction.

2. The trocar system of claim 1, wherein said trocar comprises a longitudinal port for passage of endoscopic visualization devices.

3. The trocar system of claim 1, wherein said trocar comprises a conical tip to reduce injury to said patient.

4. The trocar system of claim 1, wherein said cannula comprises a seal device adjustably located near the distal end of said cannula to form a seal between said cannula and said hole.

5. The trocar system of claim 4, wherein said seal device is rotatable with respect to said hole to improve its sealing capabilities.

6. The trocar system of claim 4, wherein said seal device is adjustably slidable with respect to said cannula for adjustment of said seal device.

7. The trocar system of claim 1, wherein each rotary blade is adapted to laterally engage the exterior tissues surrounding said incision to permit the application of a counter-traction force.

8. The trocar system of claim 7, wherein each rotary blade is adapted to extend beneath said exterior tissues in a direction substantially transverse to the direction of trocar penetration.

9. A method for establishing a port for endoscopic surgery through the superficial tissues and peritoneum of a patient's body, using the trocar system of claim 1, comprising:

incising the superficial tissue of the body;

inserting the leading edge of said retractor into said incision;

rotating said retractor such that said rotary blades puncture the tissues and remain imbedded therein;

grasping said handle and applying a lifting force to said retractor, thereby lifting said tissues away from vital organs in said patient's body to create a margin of safety above the vital organs;

sliding said trocar through said guide portion;

penetrating said peritoneum with said trocar, creating an opening therethrough; and sliding said cannula over said trocar, through said guide portion and through said opening in said peritoneum, thereby establishing said endoscopic port.

10. A trocar system adapted for use in the formation of an endoscopic port in a patient's body to provide access to internal organs, said port adapted to extend through deeper fascial tissues and peritoneum at the location of an initial incision made in overlying tissues, said system comprising:

a trocar for completely penetrating said deeper fascial tissues and peritoneum to form a hole therethrough; a cannula for surrounding said trocar and forming said port in said hole upon removal of said trocar; and a lifting device adapted for insertion prior to penetration by said trocar, for lifting said deeper fascial tissues in a direction substantially away from said internal organs, said lifting device comprising:

a body for insertion into said incision and for penetrating said overlying tissues and said deeper fascial tissues;

an opening extending completely through said body to permit the passage of said trocar and cannula; and a distal end on said body comprising at least one blade extending from said distal end of said body, said blade having a sharp distal tip and a proximal end, said blade being mounted on said body solely at said proximal end and being exposed along its entire length from said proximal end to said distal tip in order to permit said blade to pass through a perforation in said overlying tissues formed by said sharp distal tip.

11. A trocar system for assisting in the establishment of a port in a patient's body for endoscopic surgery, comprising:

a trocar for penetrating the exterior tissues and peritoneum of said patient to produce a hole therethrough;

a cannula for surrounding said trocar and forming said port in said hole upon removal of said trocar;

a retractor for penetrating the exterior tissues of said patient to allow said tissues to be lifted away from vital organs thereof, whereby the penetration of said trocar can be better controlled so as to avoid accidental injury to said vital organs;

said retractor comprising:

a hollow guide portion for receiving said cannula and said trocar and for guiding the direction of penetration of said trocar, said guide portion being slidable with respect to said cannula and said trocar, and having a distal end;

a leading edge comprising at least one blade extending distally past the terminal, distal end of the guide portion, said blade having an exposed sharp distal tip for puncturing the exterior tissues and a proximal end, each of said blades being mounted on said guide portion solely at said proximal end and being exposed along its entire length from said proximal end to said distal tip in order to permit said blade to pass though a perforation in said exterior tissues formed by said sharp distal tip.

12. The trocar system of claim 11, wherein said retractor further comprises at least one handle to aid in lifting said retractor and said blades imbedded in said tissues away from vital organs of a patient prior to insertion of said trocar.

13. The trocar system of claim 11, wherein said rotary blades are adapted to engage said tissues in a direction substantially transverse to the penetration of said trocar.

14. A method for establishing a port for endoscopic surgery through the superficial tissues and peritoneum of a patient's body, comprising:

incising the superficial tissue of the body;

inserting a retractor into said incision, said retractor comprising:

a hollow guide portion for slidably receiving a trocar and a cannula and for guiding the direction of penetration of said trocar, said guide portion having a distal end; and a leading edge comprising a pair of blades extending distally past the distal end of the guide portion, each of said blades having an exposed tip which punctures the tissue making its own perforation therein;

manipulating said retractor such that said blades puncture said tissue and said blades remains imbedded in said tissue;

lifting said retractor such that said blades imbedded in said tissues lift the tissues away from vital organs in said patient's body to create a margin of safety above the vital organs;

sliding said trocar through said guide portion; penetrating said peritoneum with said trocar, creating an opening therethrough; and sliding said cannula over said trocar, through said guide portion and through said opening in said peritoneum, thereby establishing said endoscopic port.

* * * * *